(12) United States Patent
Park et al.

(10) Patent No.: US 10,030,243 B2
(45) Date of Patent: Jul. 24, 2018

(54) NANOPARTICLE TYPE OLIGONUCLEOTIDE STRUCTURE HAVING HIGH EFFICIENCY AND METHOD FOR PREPARING SAME

(71) Applicant: BIONEER CORPORATION, Daejeon (KR)

(72) Inventors: Han Oh Park, Daejeon (KR); Jeiwook Chae, Daejeon (KR); Pyoung Oh Yoon, Daejeon (KR); Boram Han, Gyeonggi-do (KR); Gi-Eun Choi, Gyeonggi-do (KR); Youngho Ko, Seoul (KR); Taewoo Kwon, Daejeon (KR); Jae Don Lee, Gyeonggi-do (KR); Sun Gi Kim, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 0 days.

(21) Appl. No.: 14/902,563

(22) PCT Filed: Jul. 4, 2014

(86) PCT No.: PCT/KR2014/006031
§ 371 (c)(1),
(2) Date: Jan. 1, 2016

(87) PCT Pub. No.: WO2015/002511
PCT Pub. Date: Jan. 8, 2015

(65) Prior Publication Data
US 2017/0152512 A1 Jun. 1, 2017

(30) Foreign Application Priority Data

Jul. 5, 2013 (KR) .................. 10-2013-0079309

(51) Int. Cl.
| | | |
|---|---|---|
| *C12N 15/113* | (2010.01) | |
| *A61K 9/51* | (2006.01) | |
| *A61K 48/00* | (2006.01) | |
| *A61K 47/48* | (2006.01) | |
| *A61K 31/713* | (2006.01) | |

(52) U.S. Cl.
CPC .......... *C12N 15/113* (2013.01); *A61K 31/713* (2013.01); *A61K 47/48023* (2013.01); *A61K 47/48907* (2013.01); *C12N 2310/14* (2013.01); *C12N 2310/3515* (2013.01); *C12N 2320/32* (2013.01); *C12N 2330/30* (2013.01)

(58) Field of Classification Search
USPC .......... 435/6.1, 6.11, 6.12, 6.13, 91.1, 91.31, 435/455, 458; 514/44; 536/23.1, 24.5
See application file for complete search history.

(56) References Cited

U.S. PATENT DOCUMENTS

| | | |
|---|---|---|
| 5,753,263 A | 5/1998 | Lishko et al. |
| 2003/0224353 A1 | 12/2003 | Stein et al. |
| 2006/0078624 A1 | 4/2006 | Zalipsky et al. |
| 2006/0166919 A1 | 7/2006 | Shepard et al. |
| 2007/0231392 A1 | 10/2007 | Wagner et al. |
| 2008/0153737 A1 | 6/2008 | Lieberman et al. |
| 2008/0227727 A1 | 9/2008 | Erez et al. |
| 2009/0047338 A1 | 2/2009 | Swamy et al. |
| 2009/0239814 A1* | 9/2009 | Manoharan ...... A61K 47/48092 514/26 |
| 2011/0206617 A1 | 8/2011 | Roy et al. |

(Continued)

FOREIGN PATENT DOCUMENTS

| | | |
|---|---|---|
| CA | 2761749 A1 | 11/2010 |
| JP | 2013102767 A | 5/2013 |

(Continued)

OTHER PUBLICATIONS

Kim, H., et al., "Polymer-Based Hybrid Materials for Gene Delivery and Silencing", "Polymer Science and Tecnology", Jun. 2012, pp. 254-259, vol. 23, No. 3.
Shigeta, K., et al., "Novel histidine-conjugated galactosylated cationic liposomes for efficient hepatocyte-selective gene transfer in human hepatoma HepG2 cells", "Journal of Controlled Release", Dec. 28, 2006, pp. 262-270, vol. 118.
Chen, P., et al., "Strand-specific 5'-O-methylation of siRNA duplexes controls guide strand selection and targeting specificity", "RNA", Dec. 19, 2007, pp. 263-274, vol. 14, No. 2.
Kim, S., et al., "Folate receptor targeted delivery of polyelectrolyte complex micelles prepared from ODN-PEG-folate conjugate and cationic lipids", "Biotechnol. Prog.", Nov. 15, 2006, pp. 232-237, vol. 23, No. 1.

(Continued)

*Primary Examiner* — Jane Zara
(74) *Attorney, Agent, or Firm* — Hultquist, PLLC; Steven J. Hultquist

(57) ABSTRACT

The present invention relates to an oligonucleotide structure and a method for preparing the same and, more particularly, to an oligonucleotide structure in which a polymer compound is linked to an oligonucleotide via a covalent bond to improve in vivo stability of the oligonucleotide and cellular delivery efficiency of the oligonucleotide; and to a method for preparing the same. The oligonucleotide structure is improved into a homogenous material, thereby solving the problem in material verification due to polydispersion characteristics occurring when a hydrophilic material linked to the oligonucleotide is a synthetic polymer; the oligonucleotide structure is easy to synthesize compared with the existing process; and the size of a double-stranded oligo RNA structure can be accurately adjusted through the control of the repetition number of a hydrophilic material block, and thus, the gene expression regulation function of the oligonucleotide does not deteriorate through the synthesis of the optimized oligonucleotide structure, and the oligonucleotide can be delivered into cells at even a relatively low-concentration dosage. Therefore, the oligonucleotide structure of the present invention can be useful as a novel type oligonucleotide delivery system as well as a tool for treating cancers, infectious diseases, and the like.

32 Claims, 18 Drawing Sheets

(56) References Cited

U.S. PATENT DOCUMENTS

| | | |
|---|---|---|
| 2012/0108803 A1 | 5/2012 | Han et al. |
| 2012/0202871 A1 | 8/2012 | Heyes et al. |
| 2014/0248336 A1 | 9/2014 | Stein et al. |
| 2014/0371432 A1 | 12/2014 | Chae et al. |
| 2015/0018540 A1* | 1/2015 | Prakash ............ C12N 15/111 536/24.5 |
| 2015/0274698 A1 | 10/2015 | Sandanayaka et al. |

FOREIGN PATENT DOCUMENTS

| | | |
|---|---|---|
| KR | 10-2007-0061770 A | 6/2007 |
| KR | 10-2009-0042297 A | 4/2009 |
| KR | 10-2010-0123214 A | 11/2010 |
| KR | 10-2012-0119212 B1 | 10/2012 |
| KR | 101224828 B1 | 1/2013 |
| KR | 10-2013-0068032 A | 6/2013 |
| WO | 2007021142 A1 | 2/2007 |
| WO | 2009045457 A2 | 4/2009 |
| WO | 2010042823 A1 | 4/2010 |
| WO | 2010108108 A2 | 9/2010 |
| WO | 2011054939 A2 | 5/2011 |
| WO | 2013059496 A1 | 4/2013 |
| WO | 2013103249 A1 | 7/2013 |

OTHER PUBLICATIONS

Jeong, J.H., et al., "siRNA Conjugate Delivery Systems", "Bioconjugate Chem.", Jan. 2009, pp. 5-14, vol. 20, No. 1.
Ambros, V., et al, "MicroRNAs and Other Tiny Endogenous RNAs in C. elegans", Current Biology, May 13, 2003, pp. 807-818, vol. 13.
Barik, S., "Silence of the transcripts: RNA interference in medicine", J Mol Med, Jul. 19, 2005, pp. 764-773, vol. 83, No. 10.
Behlke, M., "Progress Towards in Vivo Use of siRNAs", Molecular Therapy, Feb. 14, 2006, pp. 644-670, vol. 13, No. 4.
Bertrand, J., et al., "Comparison of antisense oligonucleotides and siRNAs in cell culture and in vivo", Biochemical and Biophysical Research Communications, Aug. 30, 2002, pp. 1000-1004, vol. 296.
Chiu, Y., et al., "siRNA function in RNAi: A chemical modification analysis", RNA, Sep. 2003, pp. 1034-1048, vol. 9.
Cho, K., et al., "Therapeutic Nanoparticles for Drug Delivery in Cancer", Clin Cancer Res, Mar. 1, 2008, pp. 1310-1316, vol. 14.
De Jong, W., et al., "Drug delivery and nanoparticles: Applications and hazards", International Journal of Nanomedicine, Jun. 2008, pp. 133-149, vol. 3, No. 2.
Elbashir, S., et al., "Duplexes of 21-nucleotide RNAs mediate RNA interference in cultured mammalian cells", Nature, May 24, 2001, pp. 494-498, vol. 411.
Juliano, R., et al., "Survey and Summary: Mechanisms and strategies for effective delivery of antisense and siRNA oligonucleotides", Nucleic Acids Research, Jun. 16, 2008, pp. 4158-4171, vol. 36, No. 12.
Kim, S., et al., "Local and systemic delivery of VEGF siRNA using polyelectrolyte complex micelles for effective treatment of cancer", Journal of Controlled Release, Mar. 14, 2008, pp. 107-116, vol. 129.
Opalinska, J., et al., "Nucleic-acid therapeutics: Basic principles and recent applications", Nature Reviews: Drug Discovery, Jul. 2002, pp. 503-514, vol. 1.
Pirollo, K., et al., "Does a targeting ligand influence nanoparticle tumor localization or uptake?", Trends in Biotechnology, Aug. 21, 2008, pp. 552-558, vol. 26, No. 10.
Sano, M., et al., "Effect of asymmetric terminal structures of short RNA duplexes on the RNA interference activity and strand selection", Nucleic Acids Research, Sep. 9, 2008, pp. 5812-5821, vol. 36, No. 18.
Scanlon, K., et al., "Oligonucleotide-mediated modulation of mammalian gene expression", FASEB Journal, Oct. 1995, pp. 1288-1296, vol. 9, No. 13.
Sinha, R., et al., "Nanotechnology in cancer therapeutics: bioconjugated nanoparticles for drug delivery", Mol Cancer Ther, Aug. 2006, pp. 1909-1917, vol. 5, No. 8.
Soutschek, J., et al., "Therapeutic silencing of an endogenous gene by systemic administration of modified siRNAs", Nature, Nov. 11, 2004, pp. 173-178, vol. 432, No. 7014.
Veronese, F., "Peptide and protein PEGylation: a review of problems and solutions", Biomaterials, Mar. 2001, pp. 405-417, vol. 22, No. 5.
Veronese, F., et al., "PEGylation, successful approach to drug delivery", Drug Discovery Today, Nov. 1, 2005, pp. 1451-1458, vol. 10, No. 21.
Watts, J., et al., "Chemically modified siRNA: tools and applications", Drug Discovery Today, Jul. 7, 2008, pp. 842-855, vol. 13, No. 19/20.
Xie, F., et al., "Harnessing in vivo siRNA delivery for drug discovery and therapeutic development", Drug Discovery Today, Jan. 2006, pp. 67-73, vol. 11, No. 1/2.
Zelphati, O., et al., "Mechanism of oligonucleotide release from cationic liposomes", Proc. Natl. Acad. Sci. USA, Oct. 15, 2006, pp. 11493-11498, vol. 93, No. 21.
Lee, E. S., et al., "P oly(L-histidine)PEG block copolymer micelles and pH-induced destabilization", "Journal of Controlled Release", Jul. 31, 2003, pp. 363-374, vol. 90.
Stein, D.A., et al., "Inhibition of Dengue Virus Infections in Cell Cultures and in AG129 Mice by a Small Interfering RNA Targeting a Highly Conserved Sequence", "Journal of Virology", Oct. 2011, pp. 10154-10166, vol. 35, No. 19.
Subramanya, S., et al., "Targeted Delivery of Small Interfering RNA to Human Dendritic Cells to Suppress Dengue Virus Infection and Associated Proinflammatory Cytokine Production", "Journal of Virology", Mar. 2010, pp. 2490-2501, vol. 84, No. 5.
Cho, J., et al., "Polyethylene glycol-conjugated hyaluronic acid-ceramide self-assembled nanoparticles for targeted delivery of doxorubicin", "Biomaterials", Nov. 9, 2011, pp. 1190-1200, vol. 33, No. 2012, Publisher: Elsevier.
Li, J, et al., "Targeting the brain with PEG-PLGA nanoparticles modified with phage-displayed peptides", "Biomaterials", Apr. 5, 2011, pp. 4943-4950, vol. 32, No. 2011, Publisher: Elsevier.

* cited by examiner

HEG = Hexaethylene glycol

DSC = N,N'-Disuccinimidyl carbonate

HEG = Hexaethylene glycol
DSC = N,N'-Disuccinimidyl carbonate

J or T is respectively selected from the group consisting of (G is selected from the group consisting of C, O, S and NH); i represents repetitive number of J (0 to 10); n represents repetitive number of hydrophilic material monomer(0 to 10); L is ligand, ------ is oligonucleotide; B is hydrophobic material, preferable has a structure represented below.

NANOPARTICLE TYPE OLIGONUCLEOTIDE STRUCTURE HAVING HIGH EFFICIENCY AND METHOD FOR PREPARING SAME

CROSS-REFERENCE TO RELATED APPLICATIONS

This application is a U.S. national phase under the provisions of 35 U.S.C. § 371 of International Patent Application No. PCT/KR14/06031 filed Jul. 4, 2014, which in turn claims priority of Korean Patent Application No. 10-2013-0079309 filed Jul. 5, 2013. The disclosures of such international patent application and Korean priority patent application are hereby incorporated herein by reference in their respective entireties, for all purposes.

TECHNICAL FIELD

The present invention relates to an oligonucleotide structure having high efficiency that is effectively useful for treating cancer, infectious disease, etc.

The oligonucleotide structure according to the present invention has a structure in which a hydrophilic material and a hydrophobic material are conjugated to both ends of oligonucleotide by using a simple covalent bond or a linker-mediated covalent bond so that oligonucleotide included in the oligonucleotide structure is effectively delivered into cells, wherein the structure may be converted into a nanoparticle form by hydrophobic interactions of the oligonucleotide structures in an aqueous solution.

In addition, the present invention relates to a pharmaceutical composition including the oligonucleotide structure, a method for preparing the oligonucleotide structure, and a technology for delivering oligonucleotide using the oligonucleotide structure.

BACKGROUND ART

Various types of therapeutic agents based on oligonucleotides such as antisense oligonucleotide (ASO), RNA interference (hereinafter, referred to as 'RNAi'), microRNA (miRNA), etc., have been actively developed at present.

The ASO has a function of controlling information transfer from a gene into protein by changing an intermediate metabolism of mRNA through single-stranded RNA or DNA strand, which is to achieve desired expression control of target protein by selecting base sequences that are sufficiently complementary and specifically hybridized. The ASO is sequence-specifically bonded to a target gene, which does not have an effect on expression of other genes other than the target gene. Therefore, the ASO technology is a tool that is useful for analysis of functions in vivo of the specific protein, and has a possibility of being utilized as a gene therapy with respect to specific diseases (FASEBJ. 9, 1288-1296, 1995).

miRNA (microRNA) is small RNA of a large group that is naturally produced in a subject, and at least some of them control the expression of the target gene. The miRNA is formed from approximately 70 nucleotide single-stranded hairpin precursor transcriptomes by ribonuclease dicer (Ambros et al. 2003. current biology 13(10):807-818), wherein the dicer cuts the precursor to form 21-23 nucleotide double-stranded miRNAs. In many cases, the miRNA is transcribed from some of DNA sequences of which functions have not been found yet. The miRNA is not translated into protein, but rather, the miRNAs are combined with the specific mRNAs that block the translation. It is though that the miRNAs incorrectly form base pairs with targets thereof to inhibit the translation.

Since a role of the RNAi had been found, it was found that the RNAi sequence-sequentially functions to mRNA in various kinds of mammalian cells (Silence of the transcripts: RNA interference in medicine. J Mol Med, 2005, 83: 764-773). When a long chain of double-stranded RNA is delivered to a cell, the delivered double-stranded RNA is converted into a small interfering RNA (hereinafter, referred to as 'siRNA') which is processed to 21 to 23 base pairs (bp) by an endonuclease called a Dicer. siRNA has a short chain of double-stranded RNA having 19 to 27 bases and is coupled to an RNA-induced silencing complex (RISC), whereby a guide (antisense) strand recognizes and decomposes a target mRNA to sequence-specifically inhibit the expression of the target gene (Nucleic-acid therapeutics: basic principles and recent applications. Nature Reviews Drug Discovery. 2002. 1, 503-514).

In particular, the long-chain of double-stranded RNA delivered from the outside has a problem of excessively causing a non-sequence-specific immune reaction through interferon expression in a mammal cell; however, it is found that the problem may be overcome by a short-stranded siRNA (Duplexes of 21-nucleotide RNAs mediate RNA interference in cultured mammalian cells. Nature. 2001. 411, 494-498).

However, siRNA also has a possibility of innate immune response stimulation generated through sensors present in cells, and accordingly, in order to overcome the possibility, the specific structure of the siRNA is changed or 2-methoxy substituents or 2-fluoro substituents have been developed.

A chemically synthesized siRNA has a double-stranded of about 19 to 27 base pairs (bps) and has a 2-nt(nucleotide) overhang structure at 3'-end, and in order that the double-stranded siRNA expresses an activity, it is known that the double-stranded siRNA has a structure consisting of 3'-hydroxyl group (OH) and 5'-phosphate group ($PO_4$) (Effect of asymmetric terminal structures of short RNA duplexes on the RNA interference activity and strand selection. Nucleic Acids Res 1 Oct. 2008:5812-5821). It is known that a commercialized and synthesized siRNA has a structure in which hydroxyl groups are present at both ends, and when the synthesized siRNA is delivered to a cell, siRNA 5"-end is phosphorylated by a phosphorylation kinase to express functions of siRNA (siRNA function in RNAi: A chemical modification analysis. RNA 2003. 9: 1034-1048).

Bertrand et al., found that as compared to an antisense oligonucleotide (ASO) on the same target gene, siRNA has an effect of significantly inhibiting mRNA expression in vitro and in vivo, and the corresponding effect is maintained for a long time (Comparison of antisense oligonucleotides and siRNAs in cell culture and in vivo. Biochem. Biophys. Res. Commun. 2002. 296: 1000-1004).

In addition, since siRNA is complementarily coupled to a target mRNA to sequence-specifically regulate the expression of the target gene, a mechanism of the siRNA has an advantage that a target to be capable of being applied may be remarkably increased as compared to the existing antibody-based medical product or small molecular drug. (Progress Towards in Vivo Use of siRNAs. MOLECULAR THERAPY. 2006 13(4):664-670).

Even if an oligonucleotide (siRNA, etc)-based therapeutic agent has excellent effect and variously usable range, in order to develop the siRNA as a therapeutic agent, the siRNA is required to be effectively delivered to the target cell by improving stability of siRNA and a cell delivery efficiency of siRNA (Harnessing in vivo siRNA delivery for drug discovery and therapeutic development. Drug Discov Today. 2006 January; 11(1-2):67-73).

In particular, since the oligonucleotides such as siRNA, etc., are not passed through a hydrophobic phospholipid bilayer of a cell due to negative charges thereof, it is difficult to be delivered in the cell through a simple diffusion.

In order to increase a delivery efficiency of the oligonucleotides in vivo or in vitro, various kinds of cell delivery materials have been developed. Liposomes, cationic surfactants, etc., are generally and largely used. Further, methods of using a carrier such as a method of fusing a gene in liposome, a method of using a cationic lipid or a cationic polymer, etc., a method of changing a chemical structure, that is, changing a combined basic structure of oligonucleotide to methylphosphonate, peptide nucleic acid (PNA), etc., and a method of using a conjugate have been known (Chemically modified siRNA: tools and applications. Drug Discov Today. 2008 October; 13(19-20):842-855; Mechanisms and strategies for effective delivery of antisense and siRNA oligonucleotides. Nucleic Acids Res. 2008 July; 36(12):4158-71).

Among them, a method of using a nanocarrier, that is, a method of using various polymers such as liposome, cationic polymer composite, etc., is to capture oligonucleotides in a nanocarrier by forming nanoparticles to deliver the captured oligonucleotides to cells. Among the methods of using the nanocarrier, a method of using polymeric nanoparticle, polymer micelle, lipoplex, or the like, is mainly used, wherein the lipoplex consists of cationic lipid to interact with anionic lipid of endosome of a cell, thereby inducing a destabilization effect of the endosome to deliver the siRNA into a cell (Mechanism of oligonucleotide release from cationic liposomes. Proc. Natl. Acad. Sci. USA. 1996 Oct. 15; 93(21):11493-8).

In particular, it is known that when the oligonucleotide is siRNA, chemical materials, etc., are connected to end portions of a siRNA passenger (sense) strand to provide increased pharmacokinetics characteristics, such that high efficiency may be induced in vivo (Therapeutic silencing of an endogenous gene by systemic administration of modified siRNAs. Nature. 2004 Nov. 11; 432(7014):173-8). Here, stability of the siRNA may vary depending on properties of the chemical materials bonded to ends of the siRNA sense (passenger) or antisense (guide) strand. For example, an siRNA to which a polymer compound such as polyethylene glycol (PEG) is conjugated, interacts with an anionic phosphate group of siRNA in the presence of cationic materials to form a complex, thereby being a carrier having an improved siRNA stability (Local and systemic delivery of VEGF siRNA using polyelectrolyte complex micelles for effective treatment of cancer. J Control Release. 2008 Jul. 14; 129(2):107-16). In particular, micelle consisting of polymer complexes has an extremely small size, significantly uniform distribution, and is spontaneously form, thereby being easy to manage quality of formulation and secure reproducibility, as compared to other systems used as a drug delivery vehicle, such as microsphere, nanoparticle, etc.

Further, in order to improve an intracellular delivery efficiency of siRNA, technology of using a siRNA conjugate in which hydrophilic material which is a biocompatible polymer (for example, polyethylene glycol (PEG)) is conjugated to the siRNA by a simple covalent bond or a linker-mediated covalent bond, to thereby secure stability of siRNA and have effective cell membrane permeability was developed (see Korean Patent Publication No. 883471). However, the chemical modification of the siRNA and the conjugation with the polyethylene glycol (PEG) (PEGylation) still has disadvantages that stability in a living body is low and delivery into a target tissue is not smooth.

In order to solve the disadvantages, a structure comprising double-stranded oligo RNA ('double-stranded oligo RNA structure') in which a hydrophilic material and a hydrophobic material are bonded to oligonucleotides, in particular, double-stranded oligo RNA such as siRNA, was developed, wherein the double-stranded oligo RNA structure forms a self assembled nanoparticle named a self assembled micelle inhibitory RNA (SAMiRNA™) by a hydrophobic interaction of a hydrophobic material (see Korean Patent Publication No. 1224828), the SAMiRNA™ technology has an advantage in that homogenous nanoparticles having a significantly small size are capable of being obtained as compared to the existing delivery technologies.

As a specific example of the SAMiRNA™ technology, PEG (polyethylene glycol) is used as a hydrophilic material, wherein PEG is synthetic polymer, which is used for increasing solubility of pharmaceuticals, particularly, protein, and for controlling pharmacokinetics. PEG is a polydisperse material as like all synthetic polymers, a polymer in one batch consists of the sum of different number of monomers, a molecular weight is shown in the Gaussian curve, and polydispersity index (Mw/Mn) expresses the homogeneity degree of a material. That is, when PEG has a low molecular weight (3 to 5 kDa), the polydisperse index is about 1.01, and when PEG has a high molecular weight (20 kDa), the polydisperse index is about 1.2 which is high, such that as the molecular weight is higher, the homogeneity of the material is relatively low (F. M. Veronese. Peptide and protein PEGylation: a review of problems and solutions. Biomaterials (2001) 22:405-417).

Accordingly, when the PEG is bonded to the pharmaceuticals, polydispersity characteristic of PEG is reflected on the conjugate, such that it is difficult to verify a single material. Recently, in order to overcome the problem, production of materials having a low polydispersity index by synthesizing PEG and improving purification processes is on a rising trend, but has still problems due to polydispersity characteristic of the material, particularly, when PEG is bonded to a material having a small molecular weight, there is difficulty in confirming whether or not the binding is easily performed, etc. (Francesco M. Veronese and Gianfranco Pasut. PEGylation, successful approach to drug delivery. DRUG DISCOVERY TODAY (2005) 10(21):1451-1458).

Further, the size of nanoparticles significantly affects the deliver efficiency into the target cell, when the size of nanoparticles is 50 nm or less, the nanoparticles are rapidly removed from the body via excretion, and when the size of nanoparticles is 100 nm or more, the nanoparticles are not evenly delivered into the tissue, and the effect is reduced. Therefore, it is required to form nanoparticles each having a predetermined size (Wim H De Jong and Paul J A Borm. Int J Nanomedicine. 2008 June; 3(2): 133-149.).

Therefore, the market on a novel concept of oligonucleotide delivery technique for solving polydispersity characteristic of hydrophilic materials such as PEG, etc., of themselves while maintaining the excellent effects of SAMiRNA™ according to the related art as they are, has been urgently demanded.

DISCLOSURE OF INVENTION

An object of the present invention is to provide a novel concept of nanoparticles having a small size and improved polydispersity and an oligonucleotide structure forming the nanoparticles.

Further, another object of the present invention is to provide a method for preparing the oligonucleotide structure and nanoparticles formed of the oligonucleotide structure, a pharmaceutical composition including the oligonucleotide structure, and a technology for controlling gene expression using the same.

The present inventors found that in a technology of SAMiRNA™ which is the existing self-assembled nanoparticles, when the hydrophilic material of the oligonucletide structure configuring SAMiRNA™ is blocked as a base unit including uniform monomers (the number of monomers is m) having a predetermined molecular weight and a linker as needed, the appropriate number of blocked hydrophilic materials is used as needed, the nanoparticles formed by the oligonucleotide structure have a significantly small size and remarkably improved polydispersity as compared to the existing SAMiRNA™, and completed the present invention.

1H NMR (300 MHz, DMSO-d6); 7.91~7.86 (d, 1H), 5.66~5.61 (d, 1H), 5.28~5.25 (d, 1H), 5.10~5.03 (d, 1H), 4.25~4.19 (t, 1H), 4.15~3.94 (m, 3H), 2.12~2.10 (s, 3H), 2.04~42.02 (s, 3H), 2.00~1.98 (s, 3H), 1.91~1.89 (s, 3H), 1.78~1.76 (s, 3H)

Figure 2:
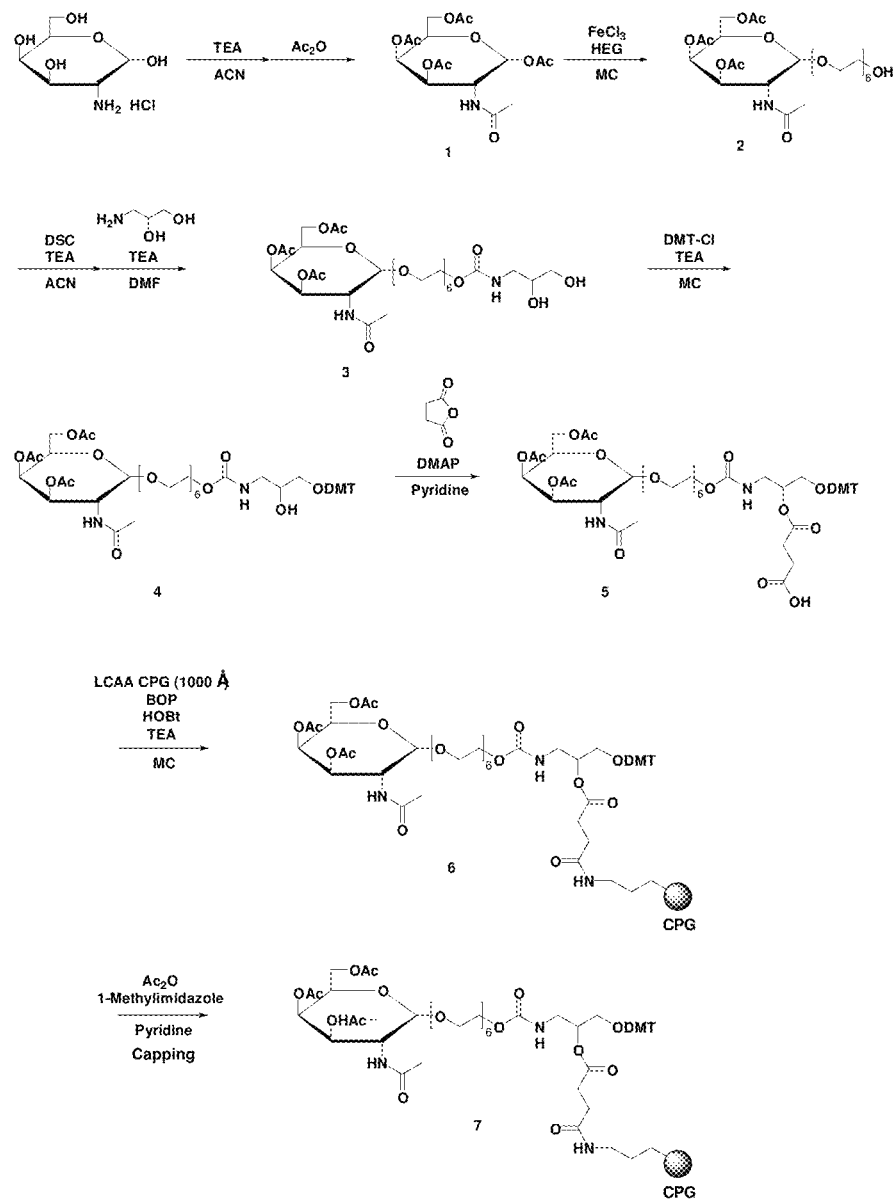
FIG. 2 shows the entire synthetic route of 3,4,6-triacetyl-1-hexa(ethylene glycol)-N-acetyl-galactosamine-CPG (Controlled Pore Glass).
Figure 6:
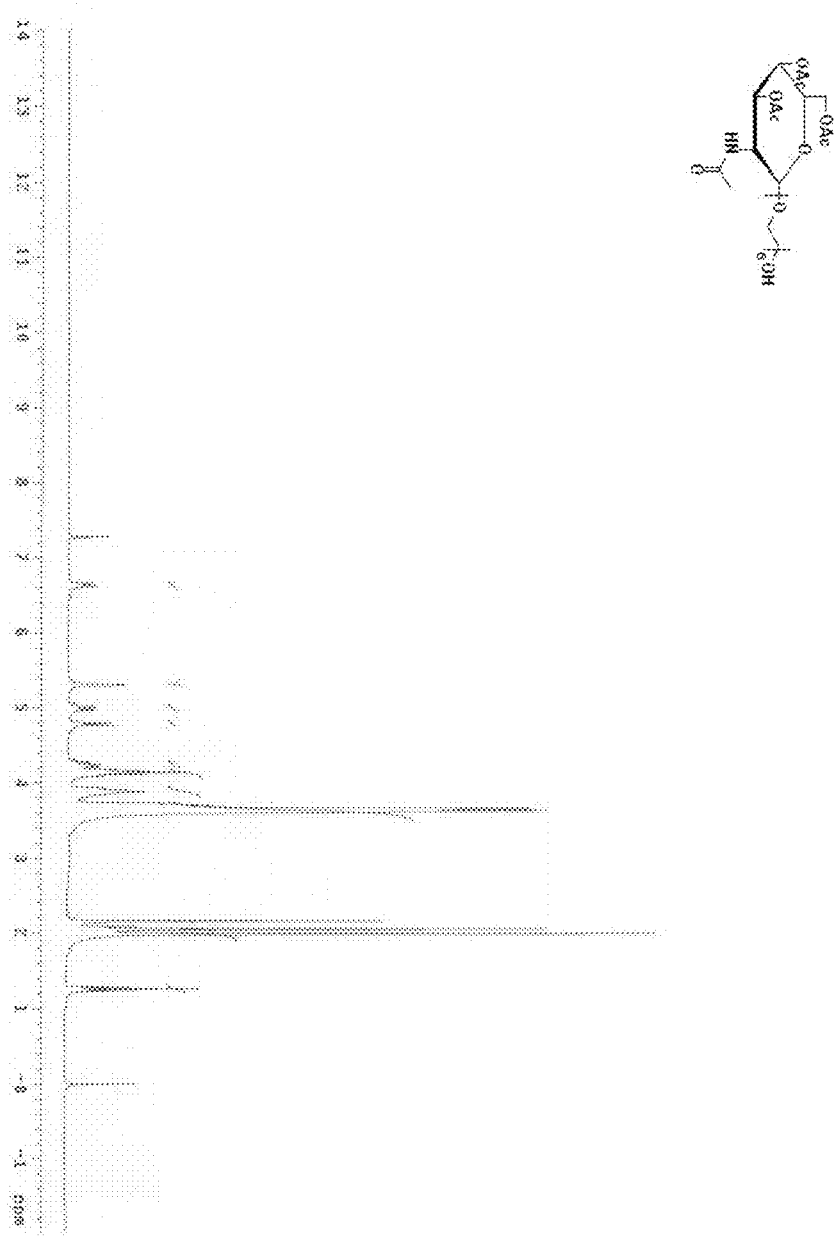

FIG. 6 shows NMR analysis results of 3,4,6-triacetyl-1-hexa(ethylene glycol)-N-acetyl galactosamine (Compound 2 of FIG. 2).

1H NMR (300 MHz, CDCl3); 6.66~6.61 (d, 1H), 5.33~5.29 (d, 1H), 5.02~4.96 (d, 1H), 4.80~4.75 (d, 1H), 4.25~4.07 (m, 2H), 3.93~3.79 (m, 2H), 3.73~3.54 (m, 24H), 2.16~2.14 (s, 3H), 2.05~2.03 (s, 3H), 1.99~1.97 (s, 6H)

Figure 7:
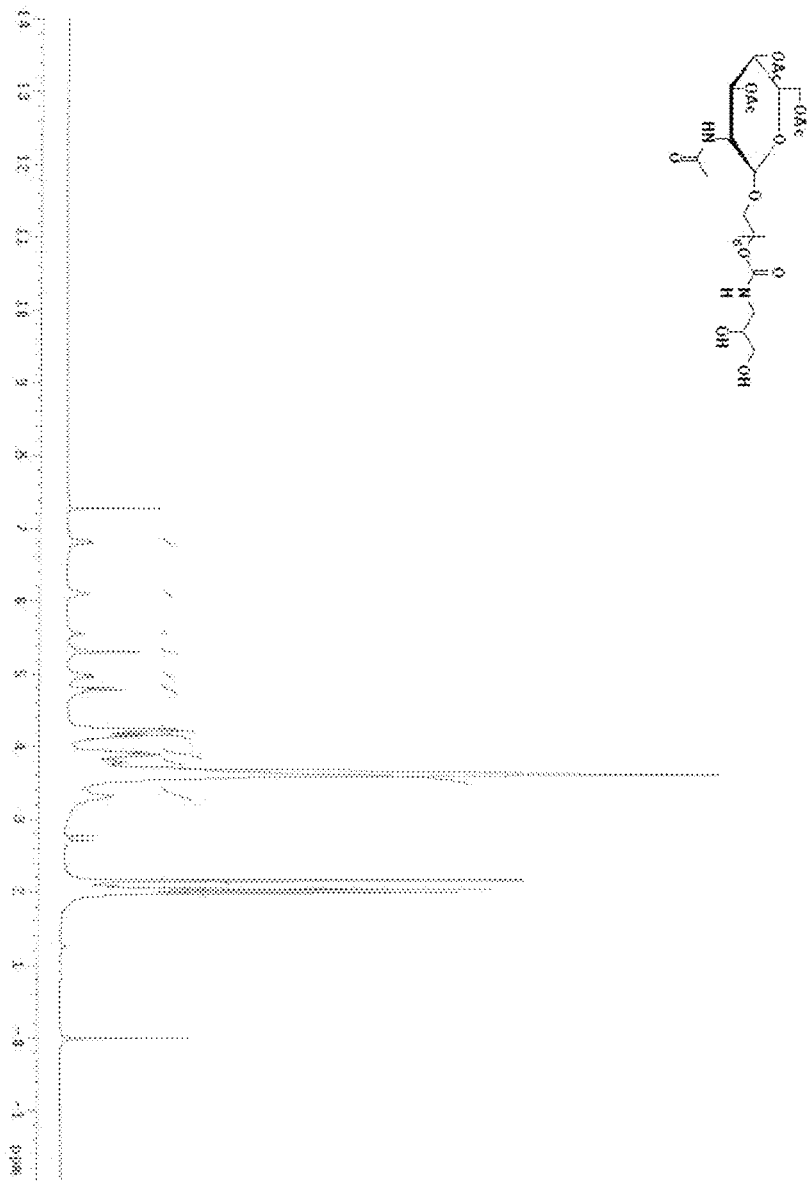

FIG. 7 shows NMR analysis results of 3,4,6-triacetyl-1-[hexa(ethylene glycol)-N'-1',2'-propanediol]-N-acetyl-galactosamine 3,4,6-triacetyl-1-[hexa(ethylene glycol)-N'-1',2'-propanediol]-N-acetyl-galactosamine (Compound 3 of FIG. 2).

1H NMR (300 MHz, CDCl3); 1H NMR (300 MHz, CDCl3); 6.83~6.78 (d, 1H), 6.10~6.08 (s, 1H), 5.33~5.29 (d, 1H), 5.00~4.94 (d, 1H), 4.82~4.77 (d, 1H), 4.22~4.08 (m, 4H), 3.9~43.85 (m, 2H), 3.83~3.74 (m, 1H), 3.66~3.52 (m, 24H), 3.4~03.24 (m, 2H), 2.18~2.16 (s, 6H), 2.05~2.03 (s, 3H), 2.00~1.98 (s, 3H)

Figure 8:
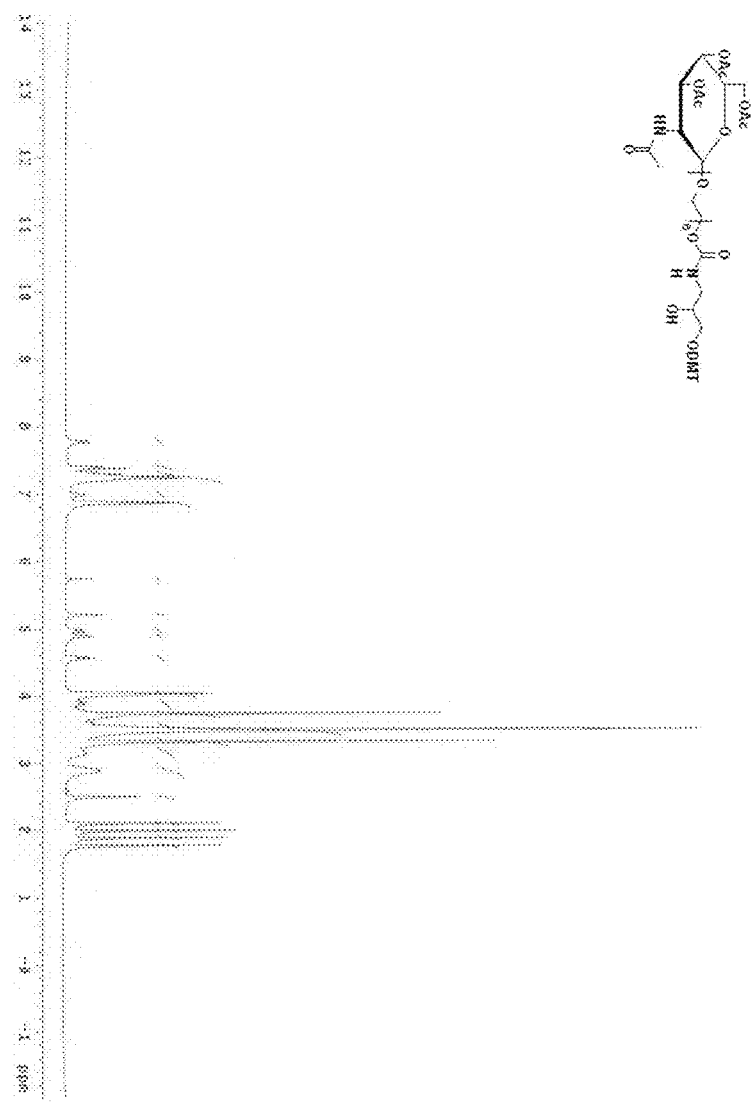

FIG. 8 shows NMR analysis results of 3,4,6-triacetyl-1-[hexa(ethylene glycol)-N'-1'-methoxy (dimethoxytrityl)-2'-propanol]-N-acetyl galactosamine (Compound 4 of FIG. 2).

1H NMR (300 MHz, DMSO-d6); 7.80~7.75 (d, 1H), 7.4~07.20 (m, 9H), 7.00~6.98 (s, 1H), 6.90~6.85 (d, 4H), 5.2~25.20 (s, 1H), 5.00~4.87 (m, 2H), 4.58~4.55 (d, 1H), 4.04~4.02 (s, 4H), 3.94~3.82 (m, 1H), 3.74~3.72 (s, 6H), 3.5~13.49 (s, 24H), 3.18~3.12 (m, 1H), 2.94~2.85 (m, 2H), 2.1~12.09 (s, 3H), 2.00~1.98 (s, 3H), 1.90~1.88 (s, 3H), 1.78~1.76 (s, 3H)

Figure 9:
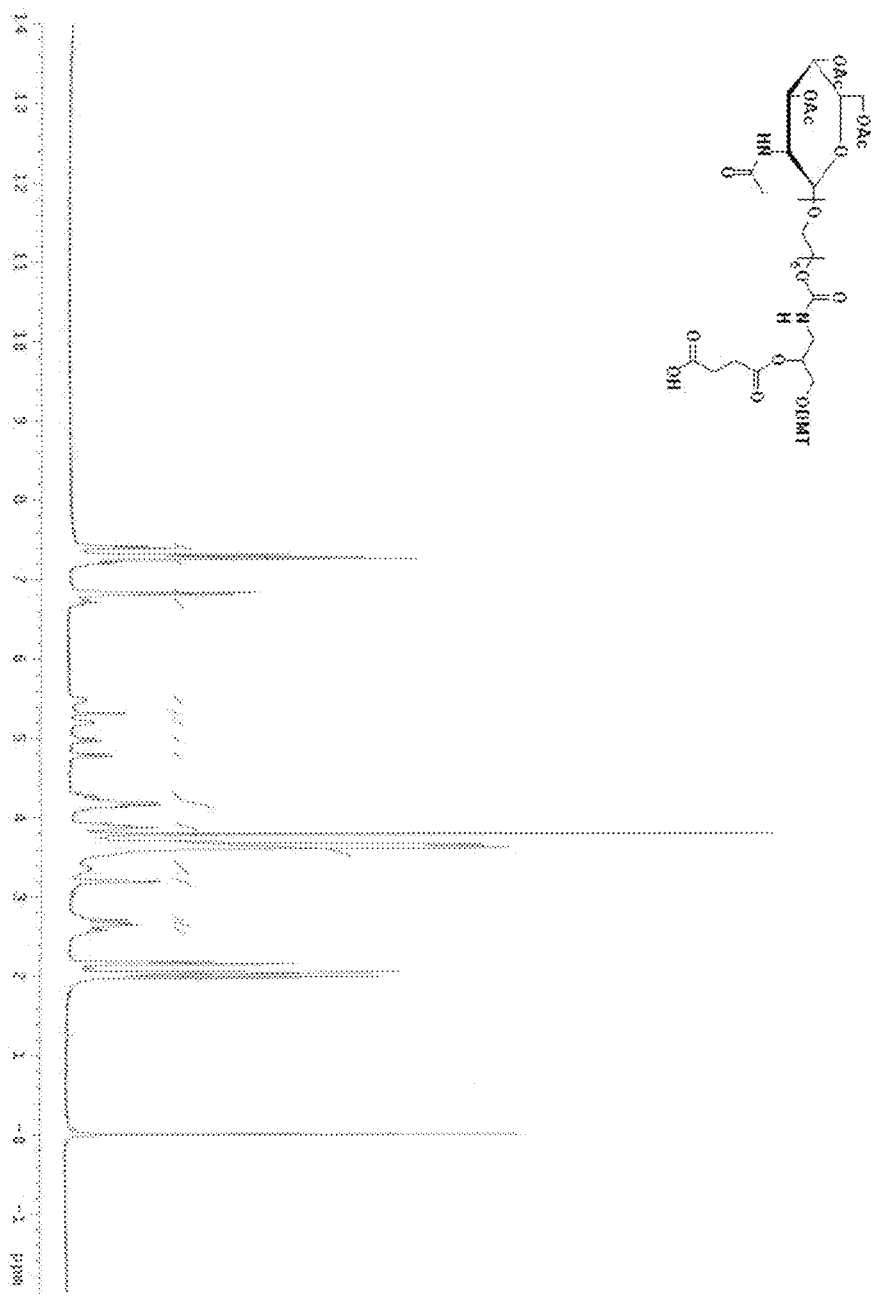

FIG. 9 shows NMR analysis results of 3,4,6-triacetyl-1-[hexa(ethylene glycol)-N'-1'-methoxy (dimethoxytrityl)-2'-propoxy (succinic acid)]-N-acetyl galactosamine (Compound 5 of FIG. 2).

1H NMR (300 MHz, CDCl3); 7.43-0.38 (d, 2H), 7.31~7.19 (m, 7H), 6.84~6.79 (d, 4H), 6.75~6.67 (t, 1H), 5.52~4.89 (m, 1H), 5.32~5.30 (s, 1H), 5.21~5.19 (s, 1H), 5.01~4.95 (d, 1H), 4.81~4.76 (d, 1H), 4.30~4.08 (m, 3H), 3.93~3.86 (m, 2H), 3.79~3.77 (s, 6H), 3.66~3.52 (m, 24H), 3.36~3.32 (m, 1H), 3.21~3.17 (d, 2H), 2.75~2.56 (m, 4H), 2.18~2.16 (s, 3H), 2.04~2.01 (m, 6H), 1.98~1.96 (s, 3H)

Figure 10:
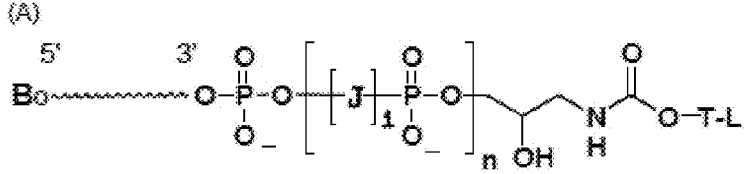
Figure 10:
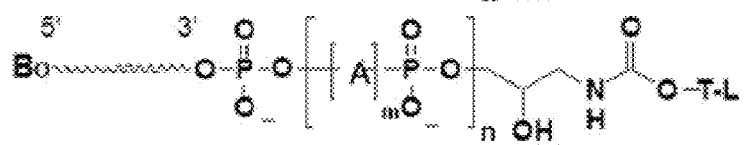
Figure 10:
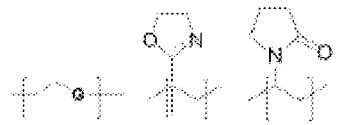
Figure 10:
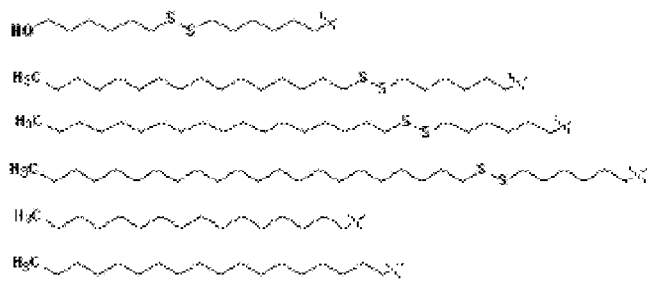
Figure 10:
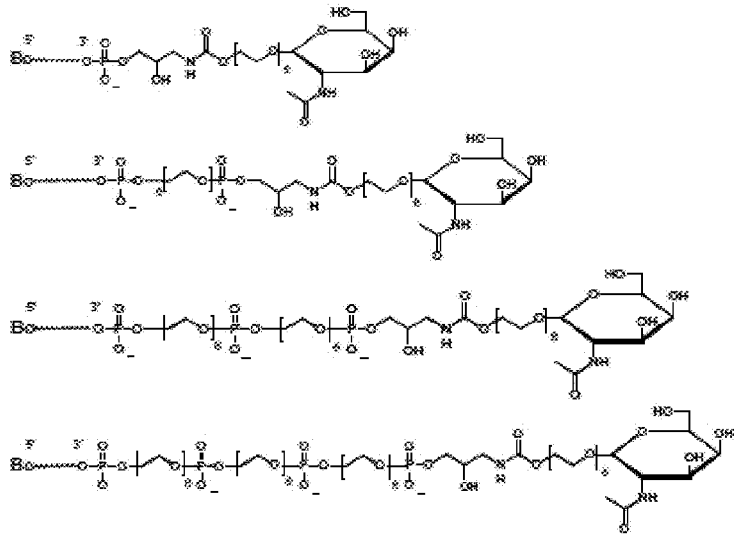

FIG. 10 shows a structure of an oligonucleotide structure to which a ligand is bonded, and as an example thereof, mono-NAG-(Hexa ethylene glycol)n-Oligo-Lipid and a structure of the lipid introduced thereinto.

(A) A structure of the oligonucleotide structure to which the ligand is bonded.
(B) A structure of mono-NAG-(Hexa ethylene glycol)n-Oligo-Lipid.

Figure 11:
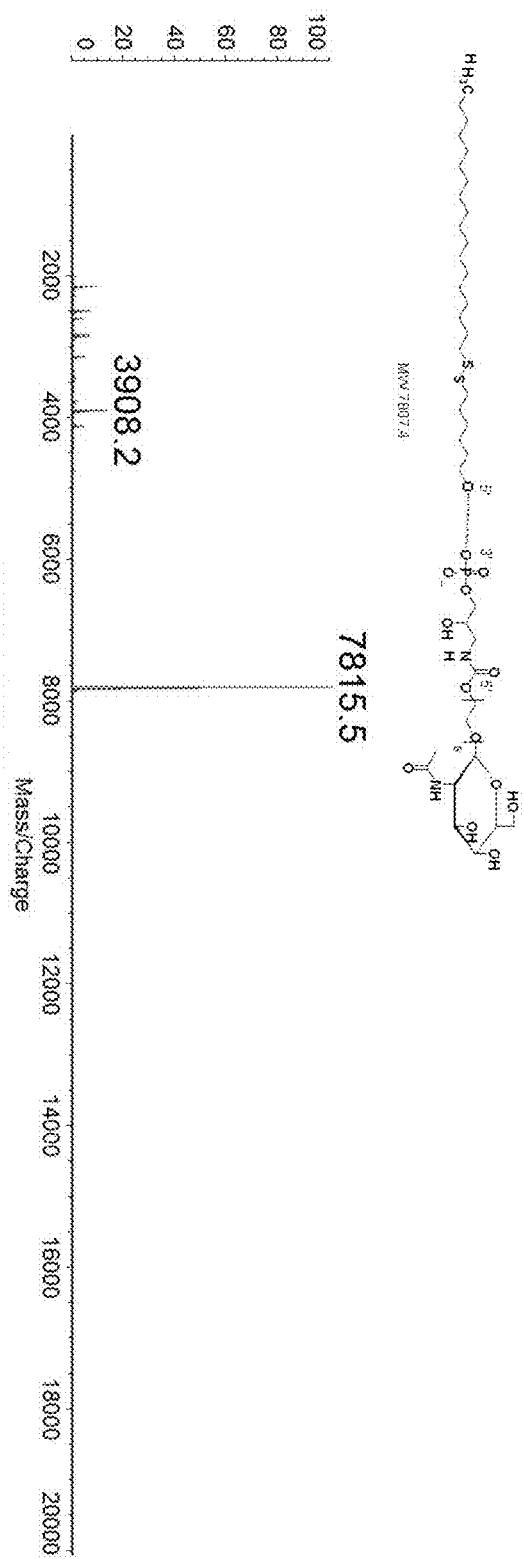

FIG. 11 shows mass spectroscopy (MALDI-TOF MS) results of mono-NAG-(HexaethyleneGlycol)1-Oligo-Lipid.
A molecular weight of (mono-NAG-(Hexaethylene Glycol)1-Oligo-Lipid (MW 7807.4)).

Figure 12:
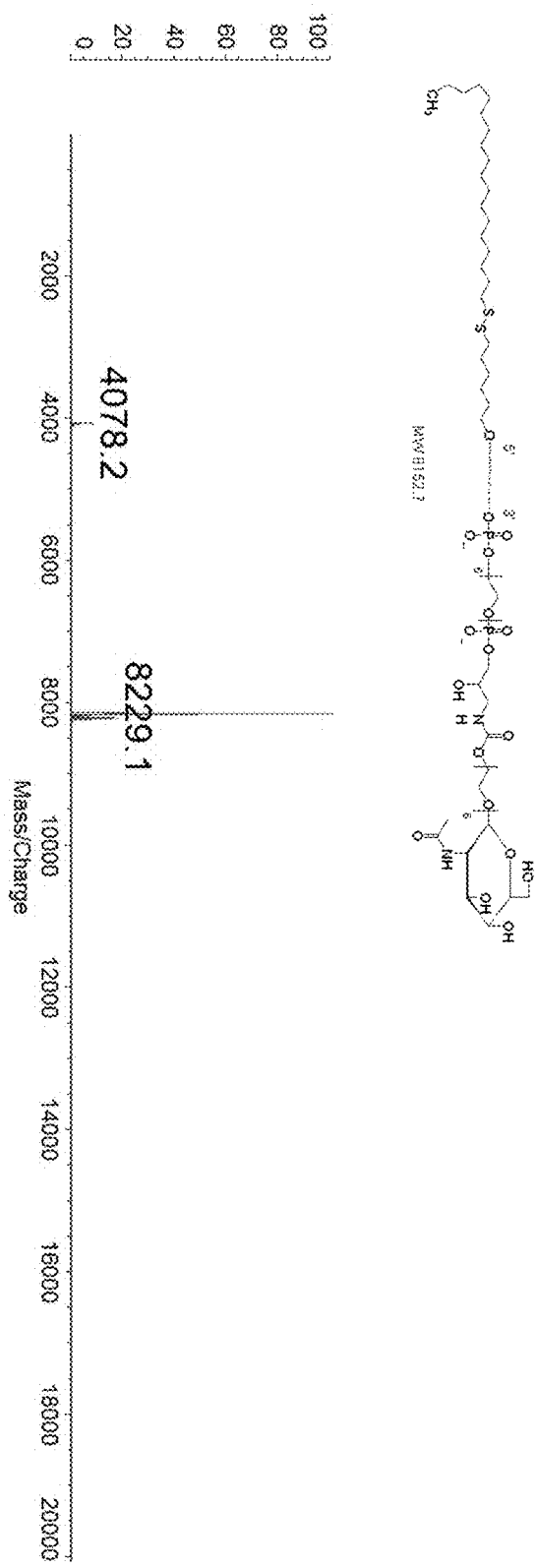

FIG. 12 shows mass spectroscopy (MALDI-TOF MS) results of mono-NAG-(HexaethyleneGlycol)2-Oligo-Lipid.
A molecular weight of (mono-NAG-(Hexaethylene Glycol)2-Oligo-Lipid (MW 8152.7)).

Figure 13:
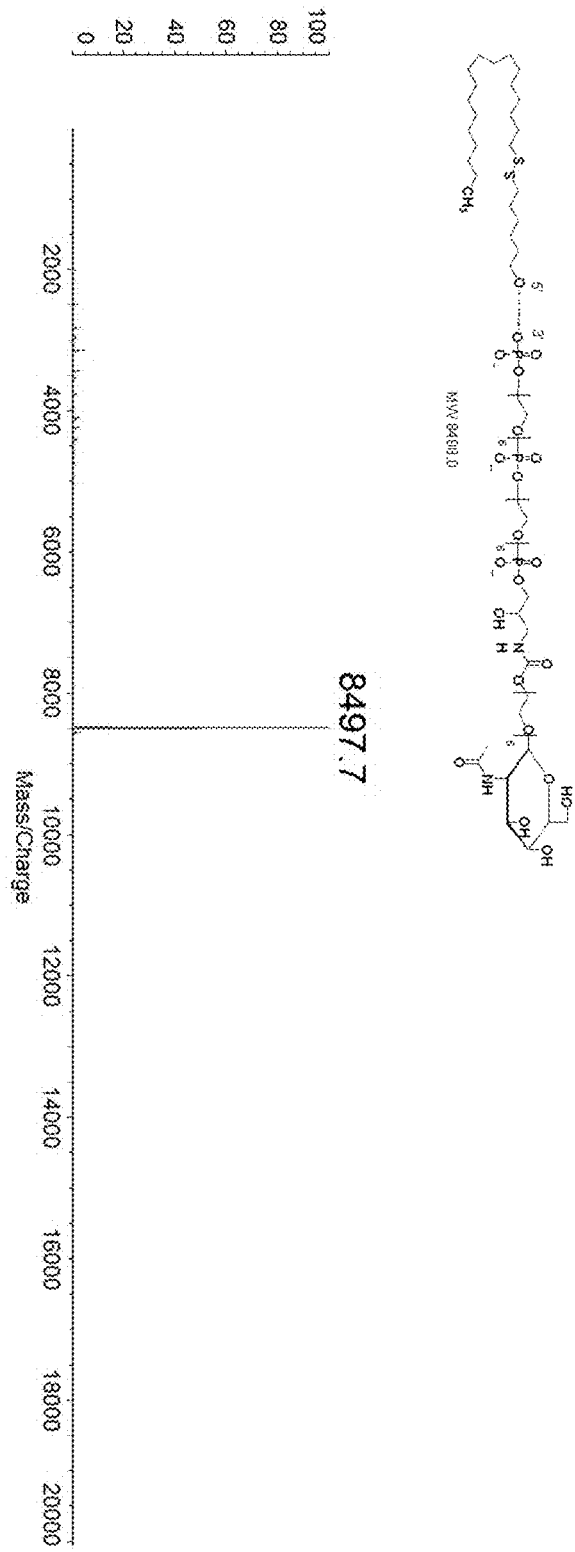

FIG. 13 shows mass spectroscopy (MALDI-TOF MS) results of mono-NAG-(HexaethyleneGlycol)3-Oligo-Lipid.
A molecular weight of (mono-NAG-(Hexaethylene Glycol)3-Oligo-Lipid (MW 8498.0)).

Figure 14:
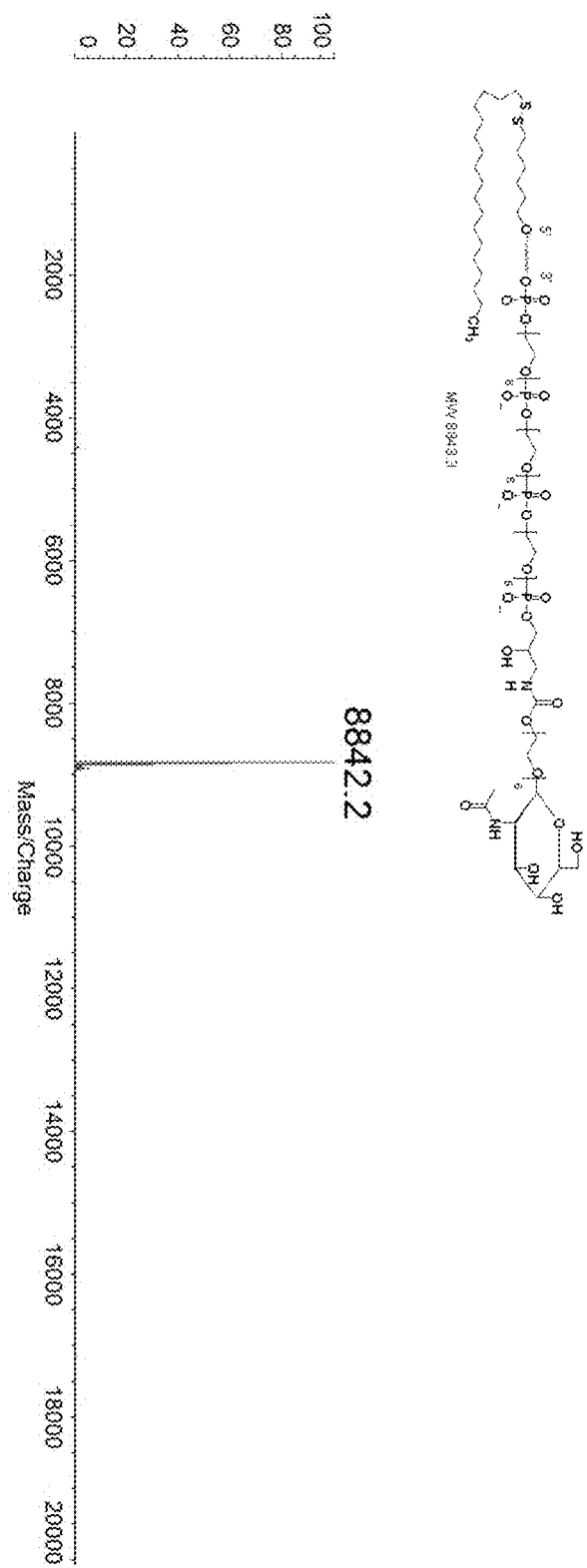

FIG. 14 shows mass spectroscopy (MALDI-TOF MS) results of mono-NAG-(HexaethyleneGlycol)4-Oligo-Lipid.
A molecular weight of (mono-NAG-(Hexaethylene Glycol)4-Oligo-Lipid (MW 8843.3)).

Figure 15:
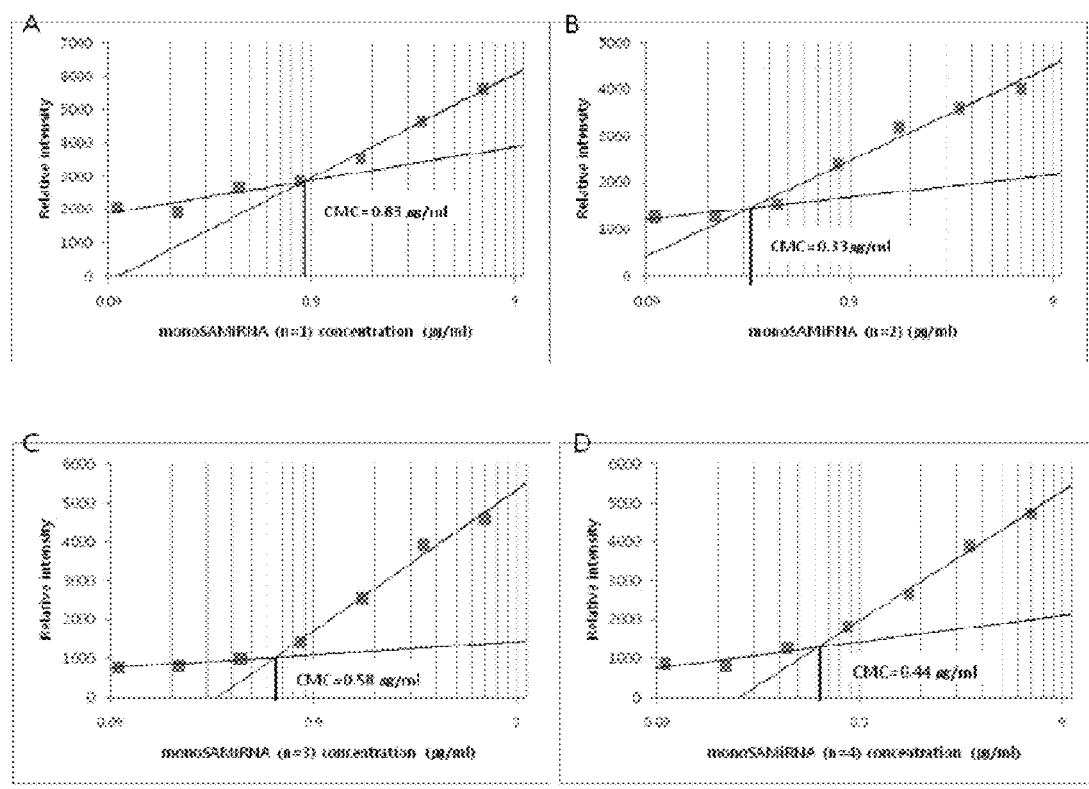

FIG. 15 is a graph obtained by measuring a critical micelle concentration of nanoparticles (SAMiRNA) of double-stranded oligo RNA structures to which hydrophilic materials each having the same molecular weight are bonded according to the present invention.

Figure 16:
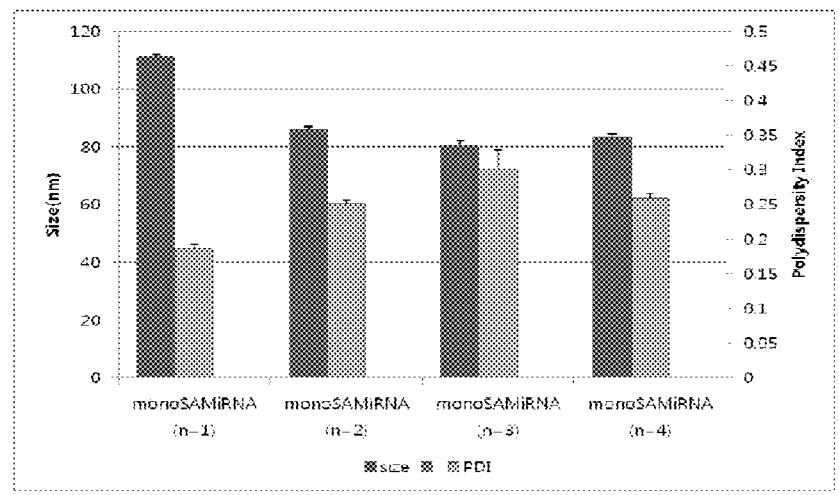

FIG. 16 is a graph obtained by measuring size and polydispersity index of the nanoparticles (SAMiRNA) of the double-stranded oligo RNA structures to which hydrophilic materials each having the same molecular weight are bonded according to the present invention.
(n means the repetition number of hydrophilic material monomer, and the nanoparticles of the double-stranded oligo RNA structure formed of the corresponding structure.)

Figure 17:
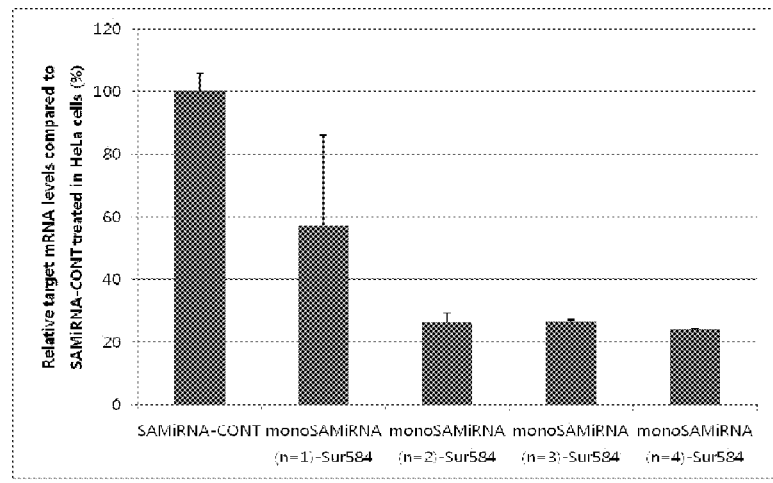

FIG. 17 shows inhibition degree of the target gene expressions in cell lines treated with the nanoparticles (SAMiRNA) of the double-stranded oligo RNA structures to which hydrophilic materials each having the same molecular weight are bonded according to the present invention.
(n means the repetition number of hydrophilic material monomer, and the nanoparticles of the double-stranded oligo RNA structure formed of the corresponding structure.)

Figure 18:
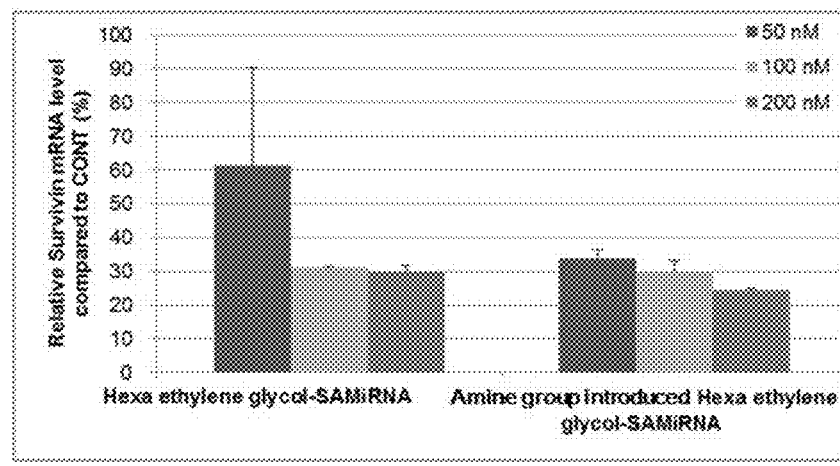

FIG. 18 is a graph of relative Survivin mRNA level compared to CONT (%), at 50 nM, 100 nM, and 200 nM, for Hexaethylene glycol-SAMiRNA and for Amine group introduced Hexaethylene glycol-SAMiRNA.

BEST MODE FOR CARRYING OUT THE INVENTION

The oligonucleotide of the present invention is a material consisting of a DNA (deoxyribonucleotide) or RNA (ribonucleotide), and means antisense oligonucleotide formed in a single-strand or a double-strand formed of complementary bindings, small interfering RNA (siRNA), small hairpin RNA (shRNA), microRNA (miRNA), miRNA inhibitor, aptamer, etc., but the present invention is not limited thereto.

In particular, when the oligonucleotide in the present invention is the double-stranded oligonucleotide, the antisense strand is a strand that is complementarily bonded to the target mRNA in the RNA-induced silencing complex (RISC) to decompose the target mRNA, thereby having RNAi activity, and the sense strand means a strand having a sequence complementary to the antisense strand. "complementary" or "complementary binding" in the present invention means that two sequences are bonded to each other to form a double-stranded structure, wherein the binding is not necessarily a perfect match binding, and may also include a mismatch in a case where some sequences are different.

Further, an miRNA mimic in the present invention is a double-stranded RNA having the same sequence and structure as miRNA present in nature, which means miRNA in a chemically synthesized form. An miRNA inhibitor means a chemically synthesized single-stranded oligonucleotide which is complementarily bonded to miRNA present in nature to inhibit the action of the corresponding miRNA.

In an exemplary embodiment, the present invention provides a novel form of oligonucleotide structure having a structure represented by the following Structural Formula (1) or Structural Formula (2).

$Q\text{-}(A_m\text{-}J)_n\text{-}X\text{-}R\text{-}Y\text{-}B$    Structural Formula (1)

$Q\text{-}(J\text{-}A_m)_n\text{-}X\text{-}R\text{-}Y\text{-}B$    Structural Formula (2)

In Structural Formulas (1) and (2), A is a hydrophilic material monomer, B is a hydrophobic material, J is a linker in which hydrophilic material monomers (the sum is m) are connected to each other or a linker in which hydrophilic material monomers (the sum is m) are connected to oligonucleotides, X and Y are each independently a simple covalent bond or a linker-mediated covalent bond, R is single-stranded or double-stranded oligonucleotide, m is an integer of 1 to 15, and n is an integer of 1 to 10, Q is $(L_i\text{-}Z_j)$ or $P\text{-}J_1\text{-}J_2$, L is a ligand specifically bonded to a receptor that promotes target cell internalization through receptor-mediated endocytosis (RME), and Z is a linker that mediates a simple covalent bond or a bond between the hydrophilic material monomer in a hydrophilic material block and the ligand, i represents an integer from 0 to 5, preferably, an integer of 0 to 3, and j means 0 or 1, provided that when i is 0, j is necessarily 0, means an amine group or a polyhistidine group, and $J_1$ and $J_2$ are independently linkers that mediate a simple covalent bond, or a bond between the amine group or the polyhistidine group with the hydrophilic material.

The "hydrophilic material block" in the present invention means a repeating unit represented by $(A_m\text{-}J)$ or $(J\text{-}A_m)$ in Structural Formulas (1) and (2).

In Structural Formulas (1) and (2), the hydrophilic material monomer A is usable without limitation as long as it meets the objects of the present invention among the monomers of the non-ionic hydrophilic polymer. The hydrophilic material monomer A is preferably a monomer selected from the following compounds (1) to (3) shown in Table 1, more preferably, a monomer of the compound (1), and G in the compound (1) may be preferably selected from $CH_2$, O, S and NH.

In particular, among the hydrophilic material monomers, the monomer of Compound (1) may have various functional groups introduced thereinto and good affinity in vivo, and induce a little immune response, thereby having excellent bio-compatibility, and further, may increase stability in vivo of the oligonucleotide included in the structures according to Structural Formulas (1) and (2), and may increase delivery efficiency, which is significantly suitable for producing the structure according to the present invention.

TABLE 1

Monomer structure of hydrophilic material preferred in the present invention

| Compound (1) | Compound (2) | Compound (3) |
|---|---|---|
| 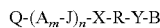<br>G is $CH_2$, O, S or NH | 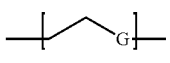 | 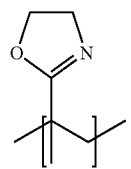 |

The hydrophilic material in Structural Formulas (1) and (2) preferably has total molecular weight of 1,000 to 2,000. Therefore, for example, when hexaethylene glycol represented by Compound (1), that is, a material in which G is O, and m is 6, is used in Structural Formulas (1) and (2), a molecular weight of hexaethylene glycol spacer is 344, such that the repetition number (n) is preferred to be 3 to 5.

In particular, in the present invention, the repeating unit of the hydrophilic group represented by $(A_m\text{-}J)$ or $(J\text{-}A_m)$ in Structural Formulas (1) and (2), that is, hydrophilic material block, is capable of being used in an appropriate number represented by n as needed. A, the hydrophilic material monomer, and J, the linker, included in each hydrophilic material block, may be independently the same as each other or be different from each other in each hydrophilic material block. That is, when 3 hydrophilic material blocks are used (n=3), the hydrophilic material monomer of the compound (1) is used in the first block, the hydrophilic material monomer of the compound (2) is used in the second block, the hydrophilic material monomer of the compound (3) is used in the third block, etc. That is, different hydrophilic material monomers for all hydrophilic material blocks may be used, and any one hydrophilic material monomer selected from the hydrophilic material monomers of compounds (1) to (3) may be equally used in all hydrophilic material blocks. Similarly, linkers that mediate the binding of the hydrophilic material monomer may also be same as each other or different from each other for all hydrophilic material blocks. Further, m which is the number of hydrophilic material monomers may be the same as each other or different from each other among all hydrophilic material blocks. That is, 3 hydrophilic material monomers (m=3) are connected in the first hydrophilic material block, 5 hydrophilic material monomers (m=5) are connected in the second hydrophilic material block, 4 hydrophilic material monomers (m=4) are connected in the third hydrophilic material block, etc. That is, hydrophilic material monomers each having different numbers or each having the same number may be used in all hydrophilic material blocks.

Further, in the present invention, the linker (J) is preferably selected from the group consisting of $PO_3^-$, $SO_3$ and $CO_2$, but the present invention is not limited thereto. It is obvious to a person skilled in the art that any linker may be used depending on the used hydrophilic material monomer, etc., as long as it meets the objects of the present invention.

Some or all of the hydrophilic material monomer may be modified to have functional groups required for binding with other materials such as a target specific ligand, etc., as needed.

The hydrophilic material block may be bonded to any position of 3' end or 5' end of the single strand oligo, and may be bonded to any position of 3' end or 5' end of the sense strand or the antisense strand of the double-stranded oligo.

The hydrophobic materials B in Structural Formulas (1) and (2) form the nanoparticles formed of the oligonucleotide structures of Structural Formulas (1) and (2) through a hydrophobic interaction. The hydrophobic material preferably has a molecular weight of 250 to 1,000, and may include a steroid derivative, a glyceride derivative, glycerol ether, polypropylene glycol, $C_{12}$ to $C_{50}$ unsaturated or saturated hydrocarbon, diacylphosphatidylcholine, fatty acid, phospholipid, lipopolyamine, etc., but the present invention is not limited thereto. It is obvious to a person skilled in the art that any hydrophobic material may be used as long as it meets the objects of the present invention.

The steroid derivative may be selected from the group consisting of cholesterol, cholestanol, cholic acid, cholesteryl formate, cholestanyl formate, and cholesteryl amine, and the glyceride derivative may be selected from mono-, di- and tri-glyceride, etc., wherein the fatty acid of the glyceride is preferred to be $C_{12}$ to $C_{50}$ unsaturated or saturated fatty acid.

In particular, among the hydrophobic materials, saturated or unsaturated hydrocarbon or cholesterol is preferred since it is easily capable of being bonded in a synthetic step of the oligonucleotide structure according to the present invention, and $C_{24}$ hydrocarbon, particularly, tetradocosane including a disulfide bond is the most preferred.

The hydrophobic material is bonded to the opposite end (distal end) of oligonucleotide bonded to the hydrophilic material block, and may be bonded to any position of the sense strand or the antisense strand of the double-stranded oligo.

The oligonucleotide (R) in the present invention may include a double-stranded or single-stranded siRNA or shRNA, antisense microRNA mimic, microRNA inhibitor, antisense oligonucleotides (ASO), etc., without limitation, and in particular, the double-stranded siRNA is more preferred.

When the double-stranded oligonucleotides such as double-stranded siRNA, miRNA, etc., are used, the sense strand and/or the antisense strand of the double-stranded oligonucleotide consists of 15 to 40, preferably 19 to 31 nucleotides, and in particular, it is preferred to bind at least one phosphate group, preferably one to three phosphate groups to 5' end of the antisense strand.

Further, the oligonucleotide has various modifications for providing resistance of nuclease and decreasing a non-specific immune stimulation in order to improve stability in vivo, wherein the modification may be one or more combinations selected from modification in which —OH group at 2' carbon in a sugar structure in one or more nucleotides is substituted with —CH$_3$(methyl), —OCH$_3$ (methoxy), —NH$_2$, —F (fluorine), —O-2-methoxyethyl, —O-propyl, —O-2-methylthioethyl, —O-3-aminopropyl, —O-3-dimethylaminopropyl, —O—N-methylacetamido or —O-dimethylamidooxyethyl; modification in which oxygen in a sugar structure in nucleotides is substituted with sulfur; and modification to phosphorothioate or boranophosphate, methyl phosphonate bindings from nucleotides bindings, or may be modification to peptide nucleic acid (PNA), modification to locked nucleic acid (LNA), or modification to unlocked nucleic acid (UNA) (Crooke et al., Ann. Rev. Med. Vol. 55: pp 61-65 2004, U.S. Pat. Nos. 5,660,985, 5,958,691, 6,531,584, 5,808,023, 6,326,358, 6,175,001 Braasch D. A. et al., Bioorg. Med. Chem. Lett. 14:1139-1143, 2003; Chiu Y. L. et al., RNA, 9:1034-1048, 2003; Amarzguioui M. et al., Nucleic Acid Res. 31:589-595, 2003, Nucleic Acids Research, 2010, Vol. 38, No. 17 5761-5773, Nucleic Acids Research, 2011, Vol. 39, No. 5 1823-1832).

Meanwhile, the tissue of the tumor is rigid to have diffusion-limitation as compared to the normal tissue, wherein this diffusion-limitation affects the movement of the waste, such as nutrients, oxygen and carbon dioxide required for tumor growth, such that the diffusion-limitation is overcome by forming the blood vessels around the tumor through angiogenesis. Blood vessels in tumor tissue formed by the angiogenesis have a leaky and defective blood vessel structure with a gap of 100 nm to 2 um, depending on types of tumors. Therefore, the nanoparticles easily pass through capillary endothelium of cancer tissue having the leaky and defective blood vessel structure as compared to organized capillaries of the normal tissue, such that it is easy to access to tumor interstitium in blood circulation process. In addition, lymphatic vessels (lymphatic drainage) are not present in the tumor tissue, such that drugs are accumulated, which refers to an enhanced permeation and retention (EPR) effect. This phenomenon in which the nanoparticles are tumor-tissue-specifically delivered by this effect, refers to passive targeting (passive targeting) (Nanoparticles for drug delivery in cancer treatment. Urol. Oncol. 2008 January-February; 26(1):57-64).

An active targeting represents a case in which a targeting moiety is bonded to the nanoparticle, and it was reported that the active targeting promotes preferential accumulation of the nanoparticles into the target tissue or improves internalization in which the nanoparticles are delivered into the target cell (Does a targeting ligand influence nanoparticle tumor localization or uptake Trends Biotechnol. 2008 October; 26(10):552-8. Epub 2008 Aug. 21). The active targeting uses materials (targeting moiety) having an ability to be capable of being bonded to carbohydrates, receptors, antigens that are specific to target cell surface or over-expressed (Nanotechnology in cancer therapeutics: bioconjugated nanoparticles for drug delivery. Mol Cancer Ther 2006; 5(8): 1909-1917).

Therefore, when a targeting moiety is provided in the oligonucleotide structure according to the present invention and the nanoparticle formed therefrom, delivery to the target cell is effectively promoted to achieve delivery to the target cell even in a relatively low concentration of dosage, thereby showing a high control function for target gene expression, and thereby preventing non-specific delivery of the oligonucleotide into other organs and cells.

Accordingly, the present invention provides structures represented by Structural Formulas (3) and (4) in which Q is ($L_i$-$Z_j$) in structures according to Structural Formulas (1) and (2), and in which the ligand (L), particularly, the ligand (L) specifically bonded to the receptor that promotes target cell internalization through receptor-mediated endocytosis (RME), is additionally included.

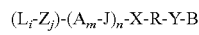  Structural Formula (3)

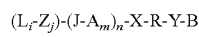  Structural Formula (4)

The ligand in Structural Formulas (3) and (4) may be preferably selected from the group consisting of a target receptor-specific antibody or aptamer, peptide having properties of RME for promoting cell internalization in the target cell-specific manner; or folate (generally, folate and folic acid are intersectionally used, and the folate in the present invention means folate in a natural state or in an activated state in a human body), chemicals such as sugar, carbohydrate, etc., including hexoamines such as N-acetyl galactosamine (NAG), etc., glucose, mannose, but the present invention is not limited thereto.

In particular, when the ligand of the present invention is sugars such as N-acetyl Galactosamine (NAG), mannose, glucose, etc., the corresponding ligand may not only complement and strengthen hydrophilicity that may be decreased depending on the repeat number of the monomer in the hydrophilic material block, but also provide a targeting effect of the nanoparticles formed of structures according to Structural Formulas (3) and (4) of the present invention, such that the nanoparticles may be easily formed.

The ligand may be either directly connected to the hydrophilic material monomer in the hydrophilic material block by a covalent bond, or may be bonded to the hydrophilic material monomer in the hydrophilic material block by a linker (Z) mediating the binding of the ligand. It is obvious to a person skilled in the art that when the ligand is covalently bonded to the hydrophilic material monomer in the hydrophilic material block by the linker (Z), any linker may be used as long as it meets the objects of the present invention. In particular, the linker preferably has any one structure selected from Compounds (4) to (7) shown in Table 2 below.

TABLE 2

Linker structure preferred in the present invention

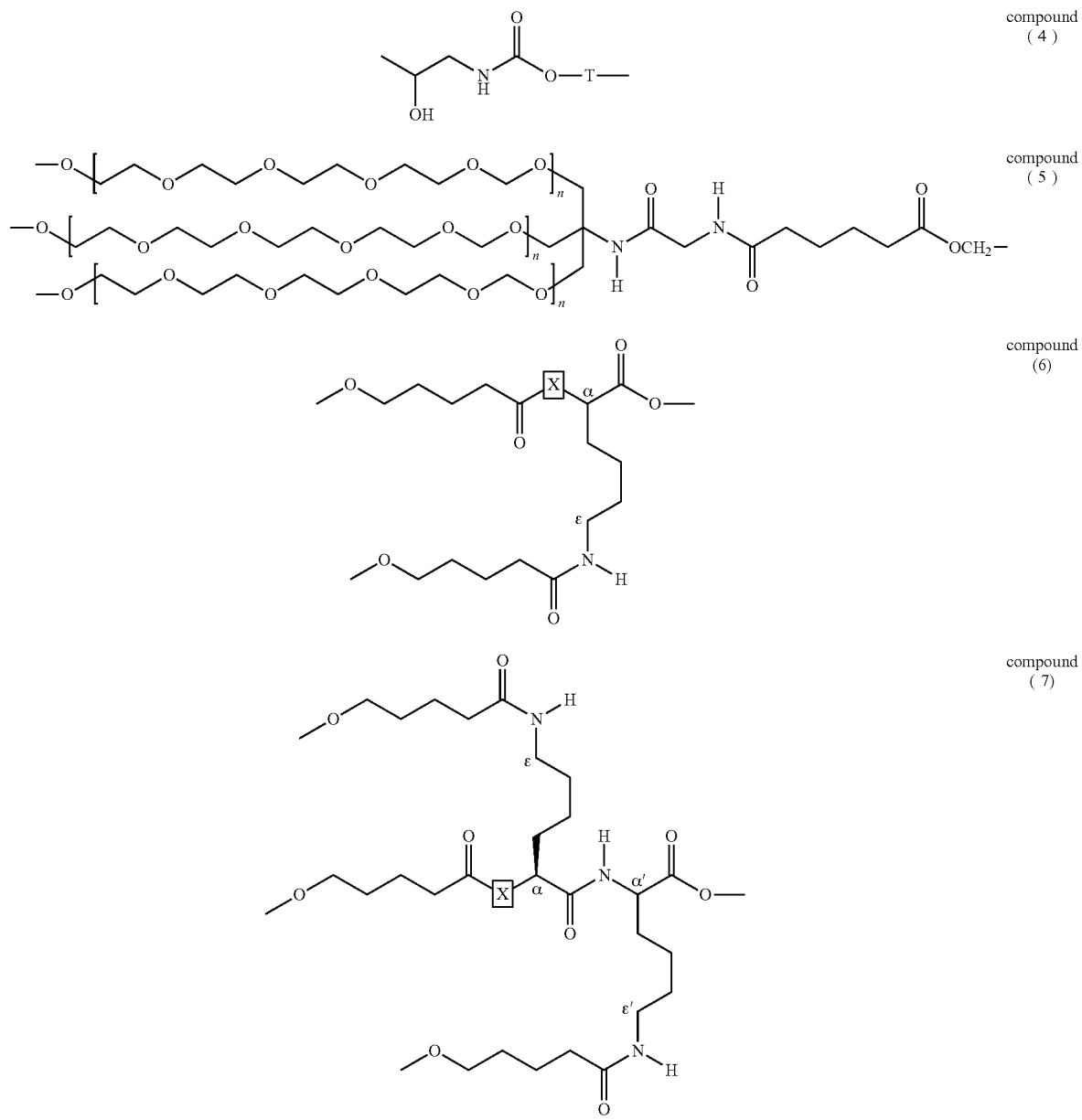

In Compound (4), T is a compound in which any one compound selected from compounds (1) to (3) is repeated 1 to 15 times, and in particular, it is preferred to repeat the compound represented by Structural Formula (1) 1 to 15 times. In Compound (4), T is bonded to the ligand, and the distal end is bonded to the hydrophilic material monomer in the hydrophilic material block or the linker.

Further, in Compounds (5) to (7), the left side of functional group is bonded to the ligand, and the right side is bonded to the hydrophilic material monomer in the hydrophilic material block, and n in Compound (5) is 0 or 1. At least one functional group that is capable of being bonded to the ligand is included in Compounds (5) to (7), such that at least one ligand binding may more improve delivery efficiency of the double-stranded oligo RNA structure according to the present invention into the target tissue.

In Structural Formulas (3) and (4), when both of i and j are 0, there is provided an oligonucleotide structure to which the ligand is not bonded, and when i is 1 and j is 0, there is provided a form in which the ligand is directly bonded to the hydrophilic material monomer in the hydrophilic material block, and when i is an integer of 1 or more, and j is 1, there is provided a linker-mediated form in which the ligand is bonded to the hydrophilic material monomer in the hydrophilic material block.

In addition, the present invention provides structures in which the amine group or the polyhistidine group is additionally introduced into the end of the hydrophilic material of structures represented by Structural Formulas 1 and 2, particularly, the distal end portion of the end bonded to siRNA, that is, structures represented by Structural Formulas 5 and 6 in which Q is $P-J_1-J_2$ in Structural Formulas (1) and (2).

$P-J_1-J_2-(A_m-J)_n-X-R-Y-B$      Structural Formula (5)

$P-J_1-J_2-(J-A_m)_n-X-R-Y-B$      Structural Formula (6)

In Structural Formulas (5) and (6), $J_1$ and $J_2$ are linkers and are each independently a simple covalent bond or are preferably selected from the group consisting of $C_{2-12}$ alkyl, alkenyl, alkynyl, $PO_3^-$, $SO_3$, and $CO_2$, but the present invention is not limited thereto. It is obvious to a person skilled in the art that any linker is usable as $J_1$ and $J_2$ as long as it meets the objects of the present invention depending on the used hydrophilic material.

Preferably, when the amine group is introduced, in Structural Formula (5), $J_2$ is preferably $PO_3^-$, and $J_1$ is preferably $C_6$ alkyl, and in Structural Formula (6), $J_2$ is preferably a simple covalent bond, and $J_1$ is preferably $C_6$ alkyl, but the present invention is not limited thereto.

In addition, when the polyhistidine group is introduced, in Structural Formula (5), $J_2$ is preferably $PO_3^-$, and $J_1$ is preferably Compound (8), and in Structural Formula (6), $J_2$ is preferably a simple covalent bond, and $J_1$ is preferably Compound (8), but the present invention is not limited thereto.

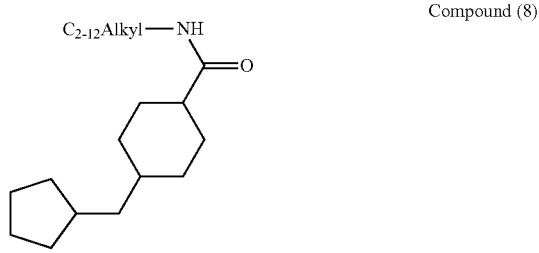

Compound (8)

The amine group in Structural Formulas (5) and (6) may be primary to tertiary amine groups, and the primary amine group is particularly preferred. The introduced amine group may be present as an amine salt. For example, the salt of the primary amine group may be present in a form of $NH_3^+$. Further, the polyhistidine group in Structural Formulas (5) and (6) preferably includes 3 to 10 histidines, more preferably, 5 to 8 histidines, and the most preferably, 6 histidines. In addition to histidine, at least one cystein may be additionally included.

The amine group or the polyhistidine group is introduced to easily perform intercellular introduction and escape from the endosome of the oligonucleotide RNA structure, and a possibility of introducing the amine group and using the polyhistidine group to easily perform the intercellular introduction and the escape from the endosome of the carriers such as Quantum dot, Dendrimer, liposome, etc., and the effect thereof, have already been reported.

Specifically, it is known that the primary amine group expressed at the end or the outside of the carrier is protonated in vivo pH to form a conjugate with a negatively charged gene by an electrostatic interaction, and the escape from the endosome is easily performed due to internal tertiary amines having a buffer effect at a low pH of the endosome after being introduced into the cells, thereby being capable of protecting the carrier from decomposition of lysosome (Gene Delivery and Expression Inhibition Using Polymer-Based Hybrid Material. *Polymer Sci. Technol.*, Vol. 23, No. 3, pp 254-259).

It is known that histidine which is one of non-essential amino acids, has an imidazole ring (pKa3 6.04) at a residue (-R) to increase a buffer capacity (buffering capacity) in the endosome and the lysosome, such that histidine expression may be used to increase an escape efficiency of the endosome in non-viral gene carriers including liposome (Novel histidine-conjugated galactosylated cationic liposomes for efficient hepatocyte selective gene transfer in human hepatoma HepG2 cells. J. Controlled Release 118, pp 262-270).

In Structural Formulas (1) to (6) in the present invention, the hydrophilic material block or the hydrophobic material is bonded to oligonucleotide by the simple covalent bond or the linker-mediated covalent bond (X or Y). The linker mediating the covalent bond is covalently bonded to the hydrophilic material block or the hydrophobic material represented by $(A_m-J)_n$ or $(J-A_m)_n$ in Structural Formulas (1) and (2) at the end of the oligonucleotide, and is not particularly limited as long as the bond that is possible to be decomposed in a specific environment is provided as needed. Therefore, any compound for the binding to activate the oligonucleotide and/or the hydrophilic material (or hydrophobic material) in preparation of the oligonucleotide structure may be used as the linker. The covalent bond may be any one of a non-degradable bond or a degradable bond. Here, examples of the non-degradable bond may include an amide bond or a phosphorylation bond, and examples of the degradable bond may include a disulfide bond, an acid degradable bond, an ester bond, an anhydride bond, a biodegradable bond or an enzymatically degradable bond, and the like, but the present invention is not necessarily limited thereto.

In Structural Formulas (1) to (6) of the present invention, when the double-stranded oligonucleotide, particularly, the double-stranded oligo RNA is used, the bondings of the double-stranded oligo RNA and the hydrophilic material block and the hydrophobic material may be various as shown in Structural Formulas 7 to 18 of Table 3 below.

TABLE 3

Types of bondings between double-stranded oligo RNA and hydrophilic and the hydrophobic material preferred in the present invention

| Structural Formula | Types | Details |
|---|---|---|
| Structural Formula (7) | (A$_m$—J)$_n$—X-3' S 5'-Y—B<br>AS | This type shows rest part of Structural Formula (1) excluding Q, and a type that hydrophilic material block is bonded to 3' end of sense strand with n repeatitively and hydrophobic material is bonded to 5' end of sense strand |
| Structural Formula (8) | (A$_m$—J)$_n$—X-3' S 5'-Y—B<br>pAS | A type that more than one phosphate group is bonded to 5' end of the antisnese strand in Structural Formula (7) |
| Structural Formula (9) | L—Z—(A$_m$—J)$_n$—X-3' S 5'-Y—B<br>AS | A type that ligand is bonded to hydrophilic material block in Structural Formula (7) |
| Structural Formula (10) | L—Z—(A$_m$—J)$_n$—X-3' S 5'-Y—B<br>pAS | A type that more than one phosphate group is bonded to 5' end of the antisense strand in Structural Formula (9) |
| Structural Formula (11) | P—J$_1$—J$_2$—(A$_m$—J)$_n$—X-3' S 5'-Y—B<br>AS | A type that amine group or polyhistidine is bonded to hydrophilic material block in Structural Formula (7) |
| Structural Formula (12) | P—J$_1$—J$_2$—(A$_m$—J)$_n$—X-3' S 5'-Y—B<br>pAS | A type that more than one phosphate group is bonded to 5' end of the antisnese strand in Structural Formula (9) |
| Structural Formula (13) | (J—A$_m$)$_n$—X-3' S 5'-Y—B<br>AS | This type shows rest part of Structural Formula (2) excluding Q, and a type that hydrophilic material block is bonded to 3' end of sense strand with n repeatitively and hydrophobic material is bonded to 5' end of sense strand |
| Structural Formula (14) | (J—A$_m$)$_n$—X-3' S 5'-Y—B<br>pAS | A type that more than one phosphate group is bonded to 5' end of the antisnese strand in Structural Formula (13) |
| Structural Formula (15) | L—Z—(J—A$_m$)$_n$—X-3' S 5'-Y—B<br>AS | A type that ligand is bonded to hydrophilic material block in Structural Formula (13) |

TABLE 3-continued

Types of bondings between double-stranded oligo RNA and hydrophilic and the hydrophobic material preferred in the present invention

| Structural Formula | Types | Details |
|---|---|---|
| Structural Formula (16) | L—Z—(J—A$_m$)$_n$—X-3' S 5'-Y—B<br>pAS | A type that more than one phosphate group is bonded to 5' end of the antisense strand in Structural Formula (15) |
| Structural Formula (17) | P—J$_1$—J$_2$—(J—A$_m$)$_n$—X-3' S 5'-Y—B<br>AS | A type that amine group or polyhistidine is bonded to hydrophilic material block in Structural Formula (13) |
| Structural Formula (18) | P—J$_1$—J$_2$—(J—A$_m$)$_n$—X-3' S 5'-Y—B<br>pAS | A type that more than one phosphate group is bonded to 5' end of the antisnese strand in Structural Formula (15) |

In Table 3, S means a sense strand of double-stranded oligo RNA, AS means an antisense strand of double-stranded oligo RNA, and pAS means an antisense strand to which a phosphate group is bonded. The remaining A, B, X, Y, L, Z, n and m are the same as being defined in Structural Formulas (1) and (2).

In particular, the oligonucleotide structure according to the present invention represented by Structural Formula (4) preferably has a structure represented by Structural Formula (19) below:

Structural Formula (19)

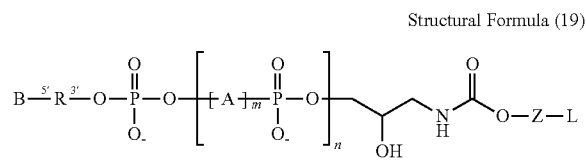

In Structural Formula (19), A is a hydrophilic material monomer, B is a hydrophobic material, L is a ligand specifically bonded to the receptor that promotes target cell internalization through receptor-mediated endocytosis (RME), Z is a linker that mediates a bond between the hydrophilic material monomer and the ligand, R is a single-stranded or double-stranded oligonucleotide, m is an integer of 1 to 15, n is an integer of 1 to 10, and A, B, L, R, etc., are the same as being defined in Structural Formula (4) of the present specification.

In particular, A is any one material selected from Compounds (1) to (3) shown in Table 1, and Z is preferably a Compound (4).

In another aspect of the present invention, the present invention provides a solid support represented by Structural Formula (20) below:

Structural Formula (20)

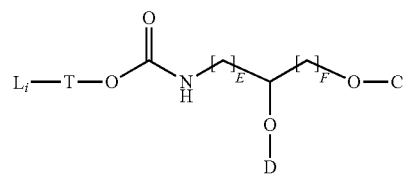

In Structural Formula (20), L is the same as being defined in Structural Formulas (3) and (4), and T is the same as being defined in Compound (4). Further, one of C and D is the solid support, the other one is dimethoxytrityl, E and F are each independently an integer of 1 to 10, and i represents 0 or 1.

In still another aspect of the present invention, the present invention provides a method for preparing oligonucleotide structures represented by Structural Formulas (1) to (4) by using the solid support represented by Structural Formula (20).

The method is to prepare the oligonucleotide structures represented by Structural Formulas (1) to (4) by using the solid support represented by Structural Formula (20) of the present invention, and when the oligonucleotide is a single strand, the method includes:

(1) covalently binding a hydrophilic material block to the solid support represented by Structural Formula (20) n-times repeatedly;

(2) synthesizing a single-stranded oligonucleotide based on the solid support to which the hydrophilic material block is bonded;

(3) covalently binding a hydrophobic material to 5' end of oligonucleotide to which the hydrophilic material block is bonded; and (4) separating the oligonucleotide structure from the solid support.

In the present invention, the solid support includes controlled pore glass (CPG), polystyrene, silica gel, cellulose paper, etc., but the present invention is not limited thereto. When the solid support is CPG, a diameter is preferably 40 to 180 μm, and preferably has a pore size of 500 to 3000 Å.

Further, when the oligonucleotide of the oligonucleotide structure of the present invention is a double-stranded RNA, the double-stranded oligonucleotide preferably consists of 19 to 31 nucleotides. The double-stranded oligonucleotide usable in the present invention may be any double-stranded oligonucleotide with respect to any gene that is used for gene therapy or gene research or that has a possibility of being used for gene therapy or gene research.

The present invention provides double-stranded oligonucleotide (RNA) structures represented by Structural Formulas (7) to (10) and (13) to (16) shown in Table 3, and a method for preparing the same. Specifically, the method is to prepare the oligonucleotide structures represented by Structural Formulas (7) to (10) and (13) to (16) by using the solid support represented by Structural Formula (20) of the present invention, and when the oligonucleotide is a double strand, the method includes:

(1) covalently binding a hydrophilic material block to the solid support represented by Structural Formula (20) n-times repeatedly;
(2) synthesizing a single-stranded RNA based on the solid support to which the hydrophilic material block is bonded;
(3) covalently binding a hydrophobic material to 5' end of RNA to which the hydrophilic material block is bonded;
(4) separating the RNA-polymer structure and a single-stranded RNA having a complementary sequence thereto from the solid support; and
(5) forming the double-stranded oligonucleotide by annealing the RNA-polymer structure and the single-stranded RNA having a complementary sequence thereto.

More preferably, the method includes:
(1) binding a hydrophilic material block based on the solid support represented by Structural Formula (20);
(2) repeating Step (1) n−1 times;
(3) synthesizing a single-stranded RNA based on the solid support to which the hydrophilic material block is bonded;
(4) binding a hydrophobic material to 5' end of the single-stranded RNA;
(5) when the synthesizing is completed, separating and purifying the RNA-polymer structure and a single-stranded RNA having a complementary sequence thereto from the solid support; and
(6) preparing the double-stranded oligo RNA structure by annealing the RNA-polymer structure and the single-stranded RNA having a complementary sequence thereto.

After Step (5) above, when the preparation is completed, whether or not desired RNA-polymer structure and single-stranded RNA are prepared, may be confirmed by purifying the reactant using high performance liquid chromatography (HPLC) and measuring a molecular weight thereof using MALDI-TOF mass spectrometry. In the preparation method, the synthesizing of the single-stranded RNA having a complementary sequence to the sequence of the single-stranded RNA synthesized in Step (3), may be performed before Step (1) or may be performed during any one step of Steps (1) to (5).

Further, when a phosphate group is bonded to 5' end of the antisense strand as shown in Structural Formula (8) or (14), the phosphate group may be bonded to 5' end of the antisense strand before or after Step (6) of the preparation method.

Further, the present invention provides double-stranded oligo RNA structures to which the ligand is bonded represented by Structural Formulas (9), (10), (15) and (16), and a method for preparing the same. Specifically, the method for preparing the double-stranded oligo RNA structures by using the solid support represented by Structural Formula (20) includes:

(1) covalently binding a hydrophilic material block based on the solid support represented by Structural Formula (20) n-times repeatedly;
(2) synthesizing a single-stranded RNA based on the solid support to which a ligand-hydrophilic material block is bonded, synthesized by Step (1);
(3) covalently binding a hydrophobic material to 5' end of the obtained material from Step (2);
(4) when the synthesizing is completed, separating and purifying the single-stranded RNA-polymer structure to which the ligand is bonded and the single-stranded RNA having a complementary sequence thereto from the solid support (CPG); and
(5) forming the double-stranded oligo RNA structure by annealing the RNA-polymer structure to which the ligand is bonded and the single-stranded RNA having a complementary sequence thereto.

After Step (5) above, when the preparation is completed, whether or not desired RNA-polymer structure to which the ligand is bonded and single-stranded RNA are prepared, may be confirmed by purifying the reactant using high performance liquid chromatography (HPLC) and measuring a molecular weight thereof using MALDI-TOF mass spectrometry. In the preparation method, the synthesizing of the single-stranded RNA having a complementary sequence to the sequence of the single-stranded RNA synthesized in Step (2), may be performed before Step (1) or may be performed during any one step of Steps (1) to (4).

Further, when a phosphate group is bonded to 5' end of the antisense strand as shown in Structural Formula (10) or (16), the phosphate group may be bonded to 5' end of the antisense strand before or after Step (6) of the preparation method.

In still another aspect, the present invention provides a method for preparing a material represented by Structural Formula (21) and oligonucleotide structures represented by Structural Formulas (1) to (4) using the material. Structural Formula (21) is different from Structural Formula (20) only in view of substituents C and D:

Structural Formula (21)

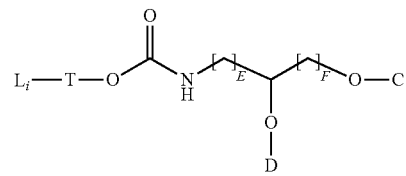

In the material represented by Structural Formula (21), one of C and D is dimethoxytrityl, and the other one is cyanoethylphosphor amidite.

The method is to prepare the oligonucleotide structures represented by Structural Formulas (1) to (4) by using the material represented by Structural Formula (21) of the present invention, and when the oligonucleotide is a single strand, the method includes:

(1) synthesizing a single-stranded oligonucleotide using a solid support to which a functional group is bonded, preferably, CPG;
(2) covalently binding a hydrophilic material monomer based on the solid support to which the oligonucleotide is bonded n-times repeatedly;
(3) covalently binding a material represented by Structural Formula (21) to 5' end of oligonucleotide to which the hydrophilic material is bonded;
(4) separating the oligonucleotide polymer structure from the solid support; and
(5) covalently binding a hydrophobic material through the functional group bonded to 3' end of the oligonucleotide structure obtained from Step (4).

Further, the method is to prepare the oligonucleotide structures represented by Structural Formulas (1) to (4) by using the material represented by Structural Formula (21) of the present invention, and when the oligonucleotide is a double strand, the method includes:

(1) synthesizing a single-stranded oligonucleotide using a solid support to which a functional group is bonded, preferably, CPG;
(2) covalently binding a hydrophilic material monomer based on the solid support to which the oligonucleotide is bonded n-times repeatedly;
(3) covalently binding a material represented by Structural Formula (21) to 5' end of oligonucleotide to which the hydrophilic material is bonded;
(4) separating the RNA-polymer structure and the single-stranded RNA having a complementary sequence thereto from the solid support;
(5) covalently binding a hydrophobic material through the functional group bonded to 3' end of the oligonucleotide structure obtained from Step (4); and
(6) forming the double-stranded oligonucleotide structure by annealing the RNA-polymer structure and the single-stranded RNA having a complementary sequence thereto.

Further, when a phosphate group is bonded to 5' end of the antisense strand, the phosphate group may be bonded to 5' end of the antisense strand before or after Step (6) of the preparation method.

In still another aspect, the present invention provides nanoparticles formed of the oligonucleotide structures represented by any one of Structural Formulas (1) to (6). The oligonucleotide is amphipathic containing both of hydrophobic materials and hydrophilic materials, wherein the hydrophilic portion consisting of n hydrophilic material blocks has affinity through an interaction such as hydrogen bond, etc., with water molecules present in the body to be toward the outside, and the hydrophobic materials are toward the inside by a hydrophobic interaction therebetween, thereby forming a thermodynamically stable nanoparticle (SAMiRNA). That is, the hydrophobic materials are positioned in the center of the nanoparticle and the hydrophilic material blocks are positioned in an outside direction of the oligonucleotide, thereby forming nanoparticles that protect the double-stranded oligo RNA (see FIG. 1). The nanoparticles as formed above may improve intracellular delivery of the oligonucleotide and improve an efficacy for controlling gene expression of oligonucletide, which is possible to be utilized for treatment of diseases.

Further, since the hydrophilic material monomer in the hydrophilic material block and the number of monomers thereof may be easily controlled, and the number of hydrophilic material blocks to be used may also be easily controlled, the hydrophilic material portions consisting of n hydrophilic material blocks in all oligonucleotide structures are the same as each other, such that the oligonucleotide structure having the hydrophilic material portion has advantages in that it is easy to perform material analysis, and as compared to the oligonucleotide structure synthesized by using the hydrophilic material through additional purification process so as to have the same molecular weight, a synthesis process is simple, and the cost may be reduced.

In addition, since the size of nanoparticles formed of the oligonucleotide structure may be regulated by controlling the repetition number of hydrophilic material blocks and hydrophilic material monomers in the hydrophilic material block, the nanoparticles formed based on the oligonucleotide may have significantly reproducible cell delivery capability.

Further, the oligonucleotide to which the ligand is bonded, wherein the ligand is particularly sugars such as N-acetyl Galactosamine (NAG), mannose, glucose, etc., and the oligonucleotide structure is represented by Structural Formula (1) or (2), may simultaneously complement and strengthen hydrophilicity that is decreased when the repetition number of hydrophilic material blocks is decreased, thereby stabilizing the formation of the nanoparticles. The nanoparticles to which the ligand is bonded as formed above may improve intracellular delivery of the oligonucleotide and improve an efficacy of oligonucleotide, which is possible to be utilized for treatment of diseases. More specific synthesis of the structure and characteristics, intracellular delivery efficiency and effects of nanoparticles formed of the oligonucleotide structures will be described by the following Examples in more detail.

Further, the present invention provides a treatment method using the oligonucleotide structures or the nanoparticles formed based on the oligonucleotide structures. Specifically, the treatment method includes preparing the nanoparticles formed of the oligonucleotide structures and administrating the nanoparticles into a body of an animal.

Further, the present invention provides a pharmaceutical composition including a pharmaceutically effective amount of nanoparticles formed of the oligonucleotide structures.

The composition of the present invention may be prepared by additionally including at least one kind of pharmaceutically acceptable carrier for administration in addition to the above-described effective components for administration. The pharmaceutically acceptable carrier is required to be compatible with the effective components of the present invention. One component selected from saline, sterile water, Ringer's solution, buffered saline, dextrose solution, maltodextrin solution, glycerol, ethanol, or a mixture of two or more thereof may be used. In addition, other conventional additives such as antioxidant, buffer, fungistat, etc., may be added thereto as needed. In addition, the composition may be prepared as a formulation for injection, such as an aqueous solution, suspension, emulsion, etc., by additionally adding diluent, dispersant, surfactant, binder and lubricant thereto. In addition, appropriate methods in the art or a method disclosed in Remington's pharmaceutical Science, Mack Publishing company, Easton Pa. may be preferably used for formulation depending on each disease or component.

The pharmaceutical composition of the present invention may be determined based on symptoms of the general patient and severity of the disease by general experts in the art. In addition, the composition may be formulated with various types such as powder, tablet, capsule, solution, injection, ointment, syrup, and the like, and may be provided as a unit-dose or a multi-dose container, for example, a sealed ampoule, bottle, and the like.

The pharmaceutical composition of the present invention may be orally or parenterally administered. Examples of an administration route of the pharmaceutical composition according to the present invention may include oral, intravenous, intramuscular, intra-arterial, intramedullary, intradural, intracardiac, transdermal, subcutaneous, intraperitoneal, intestinal, sublingual or topical administration, but the present invention is not limited thereto.

For the clinical administration as described above, the pharmaceutical composition of the present invention may be prepared as an appropriate formulation by known technology. The administration amount of the composition of the present invention may have various ranges thereof depending on weight, age, gender, health condition, diet, administration time, method, excretion rate, the severity of disease, and the like, of a patient, and may be easily determined by a general expert in the art.

The present invention provides a method of regulating gene expression in vivo or in vitro, using the oligonucleotide structure. In addition, the present invention provides a method of regulating gene expression in vivo or in vitro, using the nanoparticle containing the oligonucleotide structure.

EXAMPLES

Hereinafter, the present invention will be described in detail with reference to the following Examples. These examples are only for exemplifying the present invention, and it will be obvious to those skilled in the art that the scope of the present invention is not construed to be limited to these examples.

Example 1

Preparation of (3' N-acetyl galactosamine) CPG (controlled pore glass)

In order to prepare a double-stranded oligo RNA structure to which a ligand is bonded, N-acetyl galactosamine CPG which is a ligand material and is bondedable to the double-stranded oligo RNA structure, was prepared.

Example 1-1

Preparation of 1-hexa(ethylene glycol)-N-acetyl galactosamine-CPG (controlled pore glass) reagent In order to bind N-acetyl galactosamine (NAG) to the double-stranded oligo RNA structure, 1-hexa(ethylene glycol)-N-acetyl galactosamine-CPG (controlled pore glass) was prepared as shown in FIG. 2.

Example 1-1-1

Preparation of 1,3,4,6-tetraacetyl-NAG (Compound 1 of FIG. 2)

Starting materials, galactosamine hydrochloride (Sigma Aldrich, USA) (10 g, 46.37 mmol), acetonitrile (150 ml), and triethylamine (556.48 ml)) were mixed with each other and refluxed for 1 hour. The mixture was slowly cooled to room temperature, cooled to 0° C. using ice water, and acetic anhydride (43.83 ml, 463.70 mmol) was added dropwise. After the addition was completed, the ice water was removed, and the mixture was stirred at room temperature for 24 hours. After the reaction was completed, saturated sodium bicarbonate aqueous solution was slowly added until the pH is neutral. After pH was neutral, the mixture was stirred at room temperature for 2 hours to obtain a solid, the obtained solid was filtered, and the filtrate was sequentially washed with ethyl acetate, distilled water, and ethyl acetate. The solid was vacuum-dried to obtain 1,3,4,6-tetraacetyl-NAG (9.792 g, 56%) (see FIG. 2).

Example 1-1-2

Preparation of 3,4,6-triacetyl-1-hexa(ethylene glycol)-N-acetyl galactosamine (Compound 2 of FIG. 2)

Figure 3:
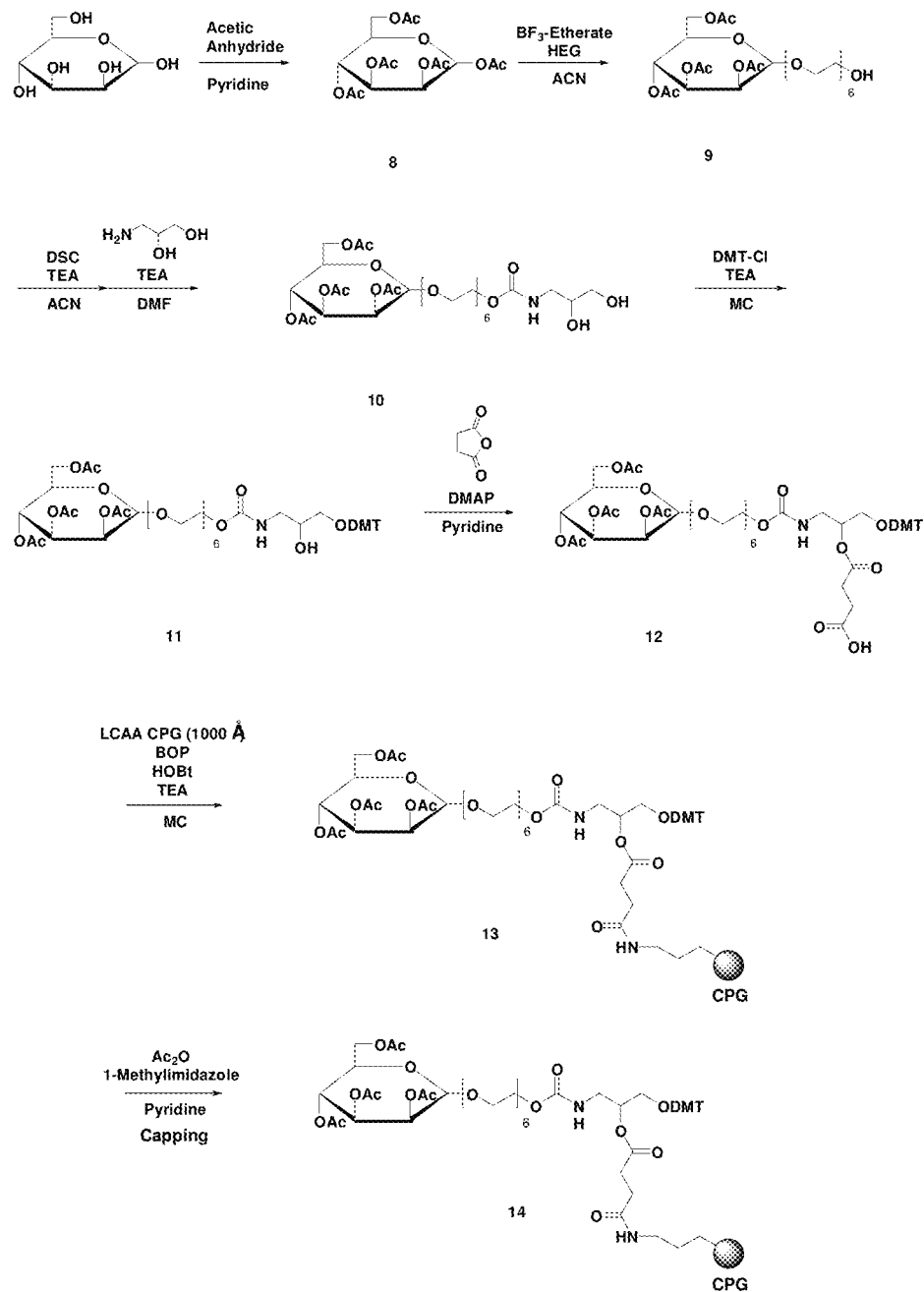
FIG. 3 shows the entire synthetic route of 2,3,4,6-tetraacetyl-1-hexa(ethylene glycol)-mannose-CPG (Controlled Pore Glass).

1,3,4,6-tetraacetyl-N-acetyl-galactosamine (6.77 g, 18.04 mmol) obtained from Example 1-1-1, iron (III) chloride (3.80 g, 23.45 mmol), and methylene chloride (200 ml) were mixed with each other and stirred at room temperature. After stirring for 10 minutes, hexa(ethylene glycol) (5.90 ml, 4.82 mmol) was added thereto and refluxed for 2 hours. After the reaction was completed, the mixture was filtered through celite, and the filtrate was washed with methylene chloride. The filtrate was concentrated under reduced pressure, and ethyl acetate and distilled water were added to extract a water layer. The obtained water layer was extracted with methylene chloride, and the organic layer was collected and dried over anhydrous magnesium sulfate and filtered. The filtrate was concentrated under reduced pressure, and vacuum-dried to obtain 3,4,6-triacetyl-1-hexa (ethylene glycol)-N-acetyl-galactosamine (2.24 g, 74.9%) (see FIG. 3).

Example 1-1-3

Preparation of 3,4,6-triacetyl-1-[hexa(ethylene glycol)-N'-1',2'-propanediol]-N-acetyl galactosamine (Compound 3 of FIG. 2)

Figure 4:
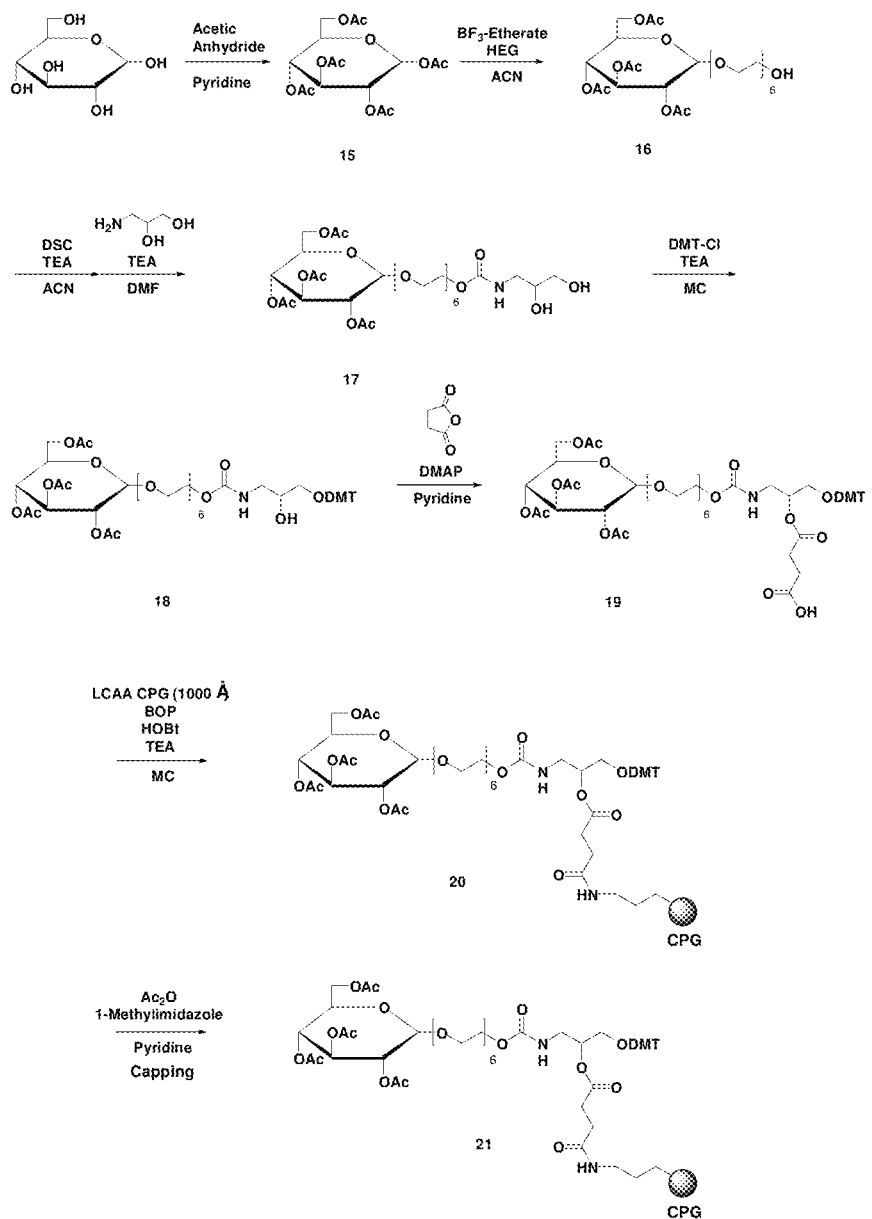
FIG. 4 shows the entire synthetic route of 2,3,4,6-tetraacetyl-1-hexa(ethylene glycol)-glucose-CPG (Controlled Pore Glass).
Figure 5:
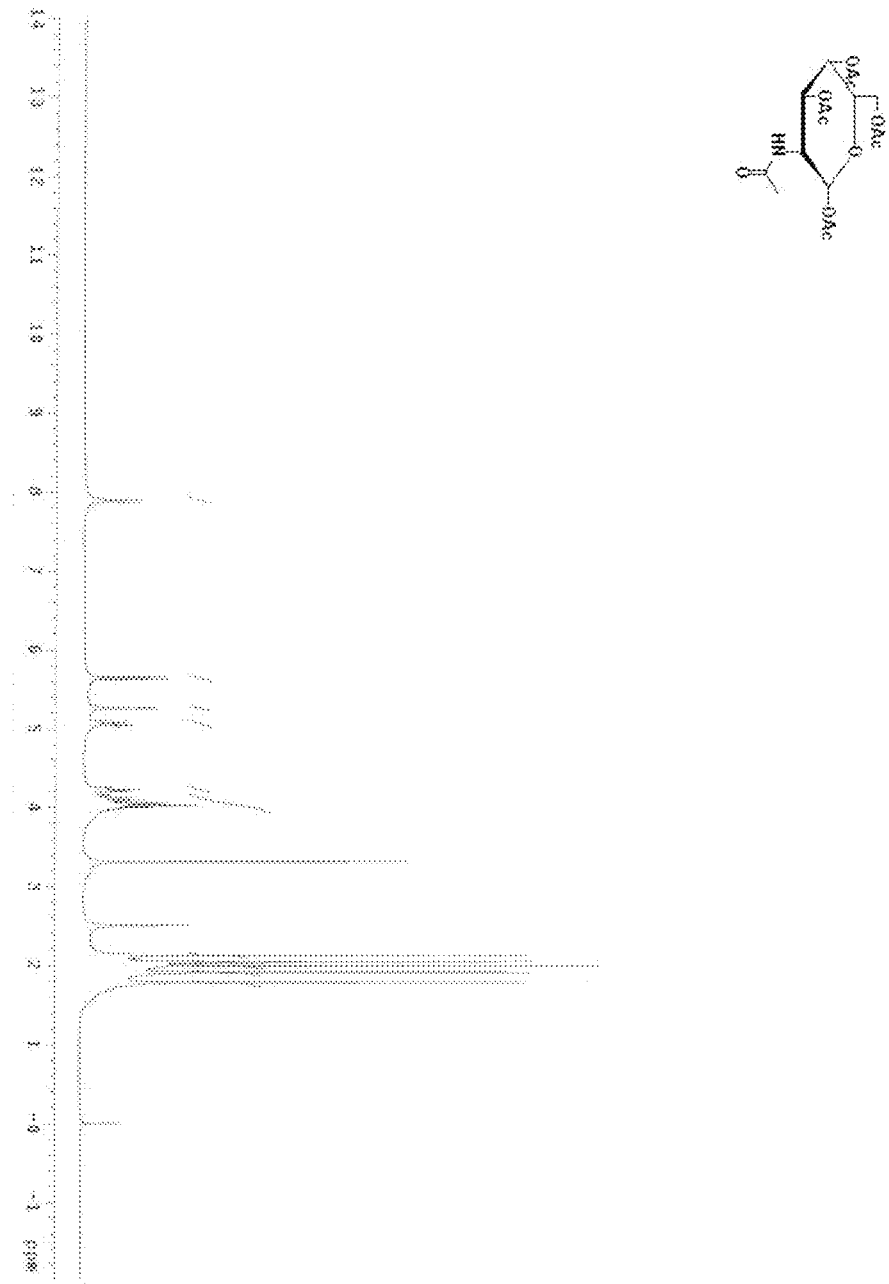
FIG. 5 shows NMR analysis results of 1,3,4,6-tetraacetyl-N-acetyl galactosamine (Compound 1 of FIG. 2).

3,4,6-triacetyl-1-hexa(ethylene glycol)-N-acetyl galactosamine (13.66 g, 22.33 mmol) obtained by Example 1-1-2 was added to acetonitrile (220 ml) and stirred. NN'-disuccinimidyl carbonate (9.15 g, 35.73 mmol), and triethylamine (9.90 ml, 71.46 mmol) were added thereto and stirred for 24 hours. 3-amino-1,2-propanediol (3.26 g, 35.73 mmol) was diluted with N,N'-dimethyl formamide (60 ml), triethylamine (4.95 ml, 35.73 mmol) was added thereto, and the mixture was added to a reaction solution and stirred for 24 hours. The mixture was concentrated under reduced pressure and vacuum-dried. The mixture was separated by a column, and the obtained solution was concentrated under reduced pressure. The obtained mixture was vacuum-dried to obtain 3,4,6-triacetyl-1-[hexa(ethylene glycol)-N'-1',2'-propanediol]-N-acetyl galactosamine (9.23 g, 56.7%) (see FIG. 4).

Example 1-1-4

Preparation of 3,4,6-triacetyl-1-[hexa(ethylene glycol)-N'-1'-methoxy(dimethoxytrityl)-2'-propanol]-N-acetyl galactosamine (Compound 4 of FIG. 2)

3,4,6-triacetyl-1-[hexa(ethylene glycol)-N'-1',2'-propanediol]-N-acetyl galactosamine (9.23 g (12.67 mmol, 1 eq))

obtained by Example 1-1-3 was added to methylene chloride (120 ml) and stirred. Triethylamine (5.27 ml (38.00 mmol, 3 eq)) was added thereto. DMT chloride (4.72 g, 13.93 mmol) diluted in methylene chloride (20 ml) was added and the mixture was stirred for 24 hours. The mixture was concentrated under reduced pressure, extracted with ethyl acetate, dried over anhydrous magnesium sulfate and filtered. The filtrate was concentrated under reduced pressure. The mixture was separated by a column, and the obtained solution was concentrated under reduced pressure. The obtained mixture was vacuum-dried to obtain desired 3,4,6-triacetyl-1-[hexa(ethylene glycol)-N'-1'-methoxy-dimethoxytrityl-2'-propanol]-N-acetyl-galactosamine (7.77 g, 59.5%).

Example 1-1-5

Preparation of 3,4,6-triacetyl-1-[hexa(ethylene glycol)-N'-1'-methoxy(dimethoxytrityl)-2'-propoxy (succinic acid)]-N-acetyl galactosamine (Compound 5 of FIG. 2)

3,4,6-triacetyl-1-[hexa(ethylene glycol)-N'-1'-methoxy (dimethoxytrityl)-2'-propanol]-N-acetyl galactosamine (7.72 g, 7.487 mmol) obtained by Example 1-1-4 was added to pyridine (70 ml), and stirred. Acetic anhydride (3.75 g, 37.486 mmol) and DMAP (0.46 g, 3.745 mmol) were added thereto, and the mixture was stirred at 60 to 70° C. for 24 hours. The mixture was concentrated under reduced pressure and vacuum-dried. The mixture was extracted with ethyl acetate. The mixture was dried over anhydrous magnesium sulfate and filtered. The filtrate was concentrated under reduced pressure. The filtrate was separated by column and the obtained solution was concentrated under reduced pressure. The obtained mixture was vacuum-dried to obtain desired 3,4,6-triacetyl-1-[hexa(ethylene glycol)-N'-1'-methoxy (dimethoxytrityl)-2'-propoxy (succinic acid)]-N-acetyl-galactosamine (7.61 g, 89.9%).

Example 1-1-6

Preparation of CPG compound before capping 3,4,6-triacetyl-1-hexa (ethylene glycol)-N-acetyl galactosamine-CPG (Compound 6 of FIG. 2)

3,4,6-triacetyl-1-[hexa(ethylene glycol)-N'-1'-methoxy (dimethoxytrityl)-2'-propoxy (succinic acid)]-N-acetyl-galactosamine (0.34 g, 0.30 mmol) obtained by Example 1-1-5 was added to long chain alkylamine-controlled pore glass (LCAA-CPG) (1000 Å) (5 g), bis-2-oxo-3-oxazolidinyl phosphoric chloride (0.2 g, 0.45 mmol), 1-hydroxybenzotriazo (0.06 g, 0.45 mmol), and methylene chloride (50 ml). Triethyl amine (0.03 ml, 2.25 mmol) was added thereto. The mixture was reacted for 24 hours. The mixture was filtered and washed with methanol. The mixture was dried to obtain a desired CPG compound (4.91 g) before capping 3,4,6-triacetyl-1-hexa (ethylene glycol)-N-acetyl galactosamine-CPG.

Example 1-1-7

Preparation of 3,4,6-triacetyl-1-hexa(ethylene glycol)-N-acetyl-galactosamine-CPG (Controlled Pore Glass) (Compound 7 of FIG. 2)

The CPG compound (4.86 g) before capping 3,4,6-triacetyl-1-hexa (ethylene glycol)-N-acetyl galactosamine-CPG obtained by Example 1-1-6, was added to pyridine (30 ml), acetic anhydride (6.02 ml, 63.70 mmol), and 1-methylimidazole (5.08 ml, 63.70 mmol), and reacted for 24 hours. The mixture was filtered and washed with methanol. The filtrate was vacuum-dried to obtain a desired compound, 3,4,6-triacetyl-1-hexa(ethylene glycol)-N-acetyl galactosamine-CPG (Controlled Pore Glass) (2.8 g).

Example 2

Preparation of Double-Stranded Oligo RNA Structure

Hereinafter, in order to inhibit Survivin, a double-stranded oligo RNA to Survivin was used. The Survivin, which is protein commonly expressed in most neoplastic tumors or transformed cell lines tested until now, is expected as an important target in cancer treatment (Survivin: a new target for anti-cancer therapy. Cancer Treat Rev. 2009 November; 35(7): 553-62).

The double-stranded oligo RNA to Survivin of the present invention consists of a sense strand of SEQ ID NO: 1 and an antisense strand having a complementary sequence thereto, and a double-stranded oligo RNA used as a control group consists of a sense strand of SEQ ID NO: 2 and an antisense strand having a complementary sequence thereto. Base sequences of the double-stranded oligo RNA used in the present Examples are as follows:

(SEQ ID NO: 1)
5'-AAG GAG AUC AAC AUU UUC A-3'

(SEQ ID NO: 2)
5'-CUU ACG CUG AGU ACU UCG A-3'

In the double-stranded oligo RNA, the double-stranded oligo RNA single strand was synthesized by a method of using β-cyanoethylphosphoramidite to connect a phosphodiester bond forming an RNA backbone structure (Polymer support oligonucleotide synthesis XVIII: use of beta-cyanoethyl-N,N-dialkylamino-/N-morpholinophosphoramidite of deoxynucleosides for the synthesis of DNA fragments simplifying deprotection and isolation of the final product. Nucleic Acids Res. 1984 Jun. 11; 12(11): 4539-57).

A desired sequence of the RNA single strand could be obtained by starting the synthesis process on the solid support (CPG) containing nucleoside bonded thereto and repeating cycles including deblocking, coupling, capping, and oxidation. The RNA 384 synthesizer (BIONEER, Korea) was used for a series of the corresponding synthesis process of the double-stranded oligo RNA.

In order to analyze physical properties of the nanoparticle formed of the double-stranded oligo RNA structure according to the repetition number of the hydrophilic material monomer forming the double-stranded oligo RNA structure, double-stranded oligo RNA structures having the following structures were prepared.

The double-stranded oligo RNA structures to which the ligand prepared in the present invention was bonded, had structures shown in Table 4 below, respectively.

TABLE 4

Details of structure to which the ligand prepared
in the present invention was bonded

| Name | Detailed structure |
|---|---|
| SAMiRNA | $C_{24}$-5' S-3' PEG-NAG<br>AS 5'-$PO_4$ |
| monoSAMiRNA (n = 1) | $C_{24}$-5' S-3'-hexaethylene glycol-NAG<br>AS 5'-$PO_4$ |
| monoSAMiRNA (n = 2) | $C_{24}$-5' S-3' (hexaethylene glycol-$PO_4^-$)$_1$-hexaethylene glycol-NAG<br>AS 5'-$PO_4$ |
| monoSAMiRNA (n = 3) | $C_{24}$-5' S-3' (hexaethylene glycol-$PO_4^-$)$_2$-hexaethylene glycol NAG<br>AS 5'-$PO_4$ |
| monoSAMiRNA (n = 4) | $C_{24}$-5' S-3' (hexaethylene glycol-$PO_4^-$)$_3$-hexaethylene glycol NAG<br>AS 5'-$PO_4$ |

In Table 4, S is a sense strand of double-stranded oligo RNA; AS is an antisense strand of double-stranded oligo RNA; $PO_4$ is a phosphate group; NAG is a ligand, N-acetyl galactosamine; PEG is a polydisperse hydrophilic material, that is, polyethylene glycol; hexamethylene glycol-$PO_3^-$ is a hydrophilic material monomer in which hexaethylene glycol is bonded through a phosphate group ($PO_3^-$); the subscript is the repetition number (n) of the hydrophilic material monomer; $C_{24}$ is a hydrophobic material, and tetradocosane including a disulfide bond; and 5' and 3' mean directivities of the double-stranded oligo RNA end.

The antisense strand of double-stranded oligo RNA structure has the same structure. The antisense strand of double-stranded oligo RNA structure was prepared by the above-described method in which a phosphodiester bond forming an RNA backbone structure is linked using β-cyanoethyl-phosphoramidite. Then, in order to bind a phosphate group to 5' end, chemical phosphorylation reagent (CPR) which is [3-(4,4" dimethoxytrityloxy)-2,2-dicarboxyethyl]propyl-(2-cyanoethyl)-(N,N-diisopropyl)-phosphoramidite was used to prepare an antisense strand of S-SAMiRNALP-$PO_4$ to which a phosphate group is bonded to 5' end. Otherwise, the antisense strand to which the phosphate group is bonded was prepared by recovering the RNA single strand from CPG and treating a phosphorylation kinase to bind the phosphate group to 5' end.

In the case of the sense strand of SAMiRNA double-stranded oligo RNA structure, the sense strand of SAMiRNA in which NAG-PEG is bonded to 3' end and tetradocosane ($C_{24}$) is bonded to 5' end was prepared by binding the hydrophilic material, that is, polyethylene glycol phosphoramidate (PEG-phosphoramidite, wherein PEG has a molecular weight (Mn) of 2000) through the above reaction using 3,4,6-triacetyl-1-hexa(ethylene glycol)-N-acetyl galactosamine-CPG prepared by Example 1, as a support, synthesizing RNA, and binding tetradocosane ($C_{24}$) including a disulfide bond to 5' end.

In the case of the sense strand of monoSAMiRNA (n=1) double-stranded oligo RNA structure, the sense strand of monoSAMiRNA (n=1) in which NAG-hexaethylene glycol is bonded to 3' end and tetradocosane is bonded to 5' end was prepared by synthesizing RNA through the above reaction using 3,4,6-triacetyl-1-hexa(ethylene glycol)-N-acetyl galactosamine-CPG prepared by Example 1, as a support, and additionally binding the hydrophobic material, that is, tetradocosane ($C_{24}$) including a disulfide bond, to 5' end.

In the case of the sense strand of monoSAMiRNA (n=2) double-stranded oligo RNA structure, the sense strand of monoSAMiRNA (n=2) in which NAG-hexaethylene glycol-(-$PO_4$-hexaethylene glycol)$_1$ is bonded to 3' end and tetradocosane is bonded to 5' end was prepared by binding the hydrophilic material monomer, that is, demethoxytrityl hexaethylene glycol phosphoramidate, through the above reaction using 3,4,6-triacetyl-1-hexa(ethylene glycol)-N-acetyl galactosamine-CPG prepared by Example 1, as a support, synthesizing RNA, and additionally binding the hydrophobic material, that is, tetradocosane ($C_{24}$) including a disulfide bond, to 5' end.

In the case of the sense strand of monoSAMiRNA (n=3) double-stranded oligo RNA structure, the sense strand of monoSAMiRNA (n=3) in which NAG-hexaethylene glycol-(-$PO_4$-hexaethylene glycol)2 is bonded to 3' end and tetradocosane is bonded to 5' end was prepared by continuously binding the hydrophilic material monomer, that is, two demethoxytrityl hexaethylene glycol phosphoramidates, through the above reaction using 3,4,6-triacetyl-1-hexa(ethylene glycol)-N-acetyl galactosamine-CPG prepared by Example 1, as a support, synthesizing RNA, and additionally binding the hydrophobic material, that is, tetradocosane ($C_{24}$) including a disulfide bond, to 5' end.

In the case of the sense strand of monoSAMiRNA (n=4) double-stranded oligo RNA structure, the sense strand of monoSAMiRNA (n=4) in which NAG-hexaethylene glycol-(-$PO_3$-hexaethylene glycol)3 is bonded to 3' end and tetradocosane is bonded to 5' end was prepared by continuously binding the hydrophilic material monomer, that is, three demethoxytrityl hexaethylene glycol phosphoramidates, through the above reaction using 3,4,6-triacetyl-1-hexa(ethylene glycol)-N-acetyl galactosamine-CPG prepared by Example 1, as a support, synthesizing RNA, and additionally binding the hydrophobic material, that is, tetradocosane ($C_{24}$) including a disulfide bond, to 5' end.

When the synthesis was completed, the RNA single strand and the RNA-polymer structure synthesized by treating 28% (v/v) ammonia in water bath at 60° C. were separated from CPG and protecting moieties were removed therefrom by a deprotection reaction, respectively. The RNA single strand and the RNA-polymer structure from which the protecting moiety was removed were treated with N-methylpyrolidon, triethylamine and triethylaminetrihydrofluoride at a volume ratio of 10:3:4 in an oven at 70° C. to remove 2' TBDMS (tert-butyldimethylsilyl). The RNA single strand, the RNA-polymer structure, and the RNA-polymer structure to which the ligand is bonded were separated from the reactants by HPLC, and molecular weights thereof were measured by MALDI-TOF mass spectrometer (SHIMADZU, Japan) to confirm whether or not base sequence and the RNA-polymer structure correspond to those to be synthesized (FIGS. 11 to 14). Then, in order to prepare each double-stranded oligo RNA structure, the sense strand and the antisense strand in an equivalent amount were mixed to each other and put into 1× annealing buffer (30 mM HEPES, 100 mM potassium acetate, 2 mM magnesium acetate (pH 7.0 to 7.5), followed by reaction in a constant temperature water bath at 90° C. for 3 minutes, and then reacted at 37° C., thereby preparing the desired SAMiRNA, monoSAMiRNA (n=1), monoSAMiRNA (n=2), monoSAMiRNA (n=3) and monoSAMiRNA (n=4), respectively. It was confirmed by electrophoresis that the produced double-stranded oligo RNA structures were annealed.

Example 3

Analysis of Physical Properties of Nanoparticles
Consisting of monoSAMiRNA

Figure 1:
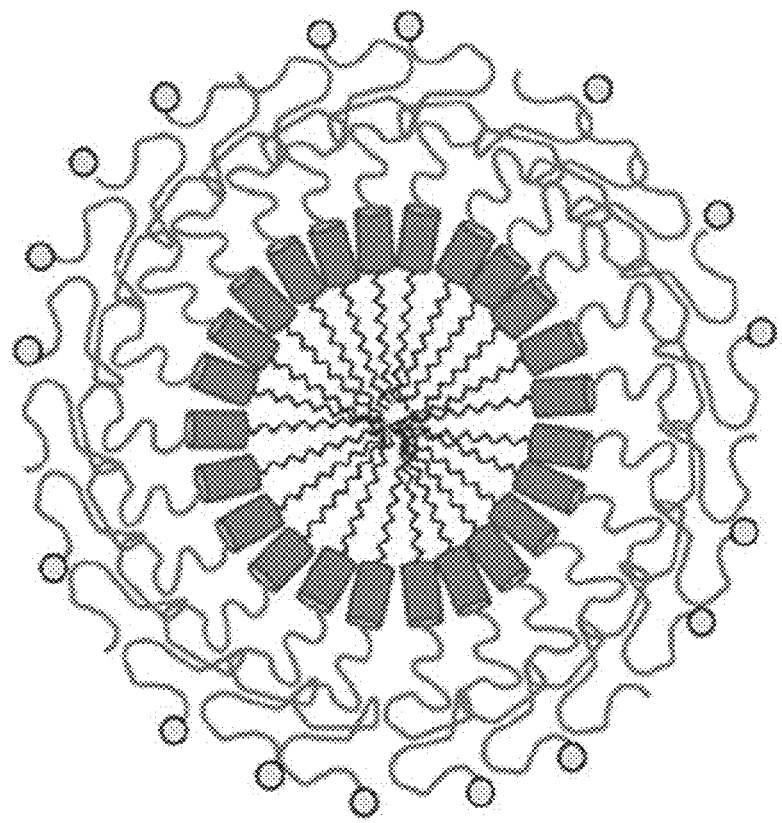
FIG. 1 is a schematic diagram of a nano-particle formed of oligonucleotide structures to which hydrophilic materials each having the same molecular weight are bonded according to the present invention.

A nanoparticle, that is, micelle, is formed by a hydrophobic interaction between the hydrophobic materials bonded to the end of the monoSAMiRNA double-stranded oligo RNA prepared by Example 2 (see FIG. 1).

Formation of the nanoparticle (SAMiRNA) consisting of the corresponding monoSAMiRNA was confirmed by analyzing the nanoparticle size and critical micelle concentration (CMC) value according to the repetition number of hydrophilic material monomers of monoSAMiRNA, and Transmission Electron Microscope (TEM).

Example 3-1

Measurement of Critical Micelle Concentration (CMC) of Nanoparticle Consisting of monoSAMiRNA An amphiphile material containing both of hydrophobic groups and hydrophilic groups in a single molecule may be a surfactant, wherein when the surfactant is dissolved into an aqueous solution, the hydrophobic groups thereof move toward the center portion to prevent the hydrophobic groups from being contacted with water and the hydrophilic groups thereof move toward the outside to form a micelle. Here, a concentration at which the micelle is initially formed is referred to as a critical micelle concentration (CMC). A method of measuring CMC using fluorescent pigment is based on property of the fluorescent pigment in which the slope of the graph curve of the fluorescence intensity is rapidly changed before/after the micelle is formed. In order to measure CMC of the nanoparticle consisting of monoSAMiRNA, 0.04 mM DPH (1,6-Diphenyl-1,3,5-hexatriene, SIGMA, USA) was prepared as the fluorescent pigment. 1 nmole/μl of monoSAMiRNA (n=1) was diluted from a concentration of 0.0977 μg/ml to the maximum of 50 μg/ml with DPBS for each step to prepare monoSAMiRNA (n=1) samples having the total volume of 180 μl. 20 μl of 0.04 mM DPH and methanol which is a solvent of DPH for a control group were added to the prepared samples, respectively, and mixed well, and treated by ultrasonic disperser (Wiseclean: DAIHAN, Korea) so that a size of the nanoparticle is homogenized (700 W; amplitude: 20%). The homogenized samples were reacted at room temperature without light for about 24 hours, and fluorescent values (excitation: 355 nm, emission: 428 nm, top read) were measured. In order to confirm relative fluorescent values among the measured fluorescent values, the fluorescent value of the sample containing DPH—the fluorescent value of the sample containing only the methanol (Y axis) at the same concentration was measured and shown as a graph with respect to log value of the treated concentration of monoSAMiRNA (n=1) (X axis). MonoSAMiRNA (n=2) and monoSAMiRNA (n=3) were measured by the same method as described above.

The fluorescent value measured for each concentration was rapidly increased while moving from a low concentration section to a high concentration section, wherein the concentration at the rapidly increased point is CMC concentration. Therefore, when drawing trend lines by dividing the low concentration section in which the fluorescent amount is not increased and the high concentration section in which the fluorescent amount is increased into several sections, an X value in an intersection of the two trend lines is CMC concentration. It was observed that the measured CMC of the nanoparticle consisting of monoSAMiRNA (n=1) was 0.83 μg/ml, which was relatively high, and the measured CMC of the nanoparticle consisting of monoSAMiRNA (n=2) was 0.33 μg/ml, which was significantly low. It was observed that the measured CMC of the nanoparticle consisting of monoSAMiRNA (n=3) was 0.58 μg/ml, and the measured CMC of the nanoparticle consisting of monoSAMiRNA (n=4) was 0.44 μg/ml (FIG. 15). Accordingly, it was confirmed that the micelle could be well-formed by the nanoparticle consisting of monoSAMiRNA even at a significantly low concentration.

Example 3-2

Preparation of Nanoparticles Consisting of monoSAMiRNA

In order to prepare homogenized nanoparticles, the monoSAMiRNA (n=1) was dissolved in 1.5 ml DPBS (Dulbecco's Phosphate Buffered Saline) at a concentration of 50 μg/ml, and the obtained mixture was freeze-dried under condition of −75° C. and 5 mTorr for 48 hours. MonoSAMiRNA (n=2), monoSAMiRNA (n=3), and monoSAMiRNA (n=4) were measured by the same method as described above.

Example 3-3

Measurement of Size and Polydispersity Index (PDI) of Nanoparticle Consisting of monoSAMiRNA A size of the nanoparticle was measured by zeta-potential measurement. Specifically, a size of the homogenized nanoparticle produced by Example 3-2 was measured by zeta-potential measurement (Nano-ZS, MALVERN, England), under conditions in which a refractive index to the material was 1.459, an absorption index was 0.001, a temperature of a solvent: DPBS was 25° C. and the corresponding viscosity and refractive index were 1.0200 and 1.335, respectively. Once measurement was conducted by a size measurement including 15 times repeats and then repeated six times. MonoSAMiRNA (n=1), monoSAMiRNA (n=2), monoSAMiRNA (n=3), and monoSAMiRNA (n=4) were measured by the same method as described above.

It was confirmed that a size of the nanoparticle consisting of monoSAMiRNA (n=1) was 111 nm and PDI of the nanoparticle consisting of monoSAMiRNA (n=1) was 0.19. It was confirmed that a size of the nanoparticle consisting of monoSAMiRNA (n=2) was about 86 nm and PDI thereof was 0.25, a size of the nanoparticle consisting of monoSAMiRNA (n=3) was about 80 nm and PDI thereof was 0.30, and a size of the nanoparticle consisting of monoSAMiRNA (n=4) was about 83 nm and PDI thereof was 0.26 (FIG. 16). As the PDI value is decreased, the corresponding particles become uniformly distributed, and thus, it could be appreciated that the nanoparticle of the present invention has a significantly uniform size.

Example 3-4

Observation of Nanoparticle Consisting of monoSAMiRNA by TEM

The nanoparticle consisting of monoSAMiRNA was observed by TEM in order to confirm the shape thereof. Specifically, the S-SAMiRNA was dissolved into DPBS so as to have the final concentration of 100 μg/ml and treated by ultrasonic disperser (Wiseclean: DAIHAN, Korea) so that a size of nanoparticle is homogenized (700 W; amplitude: 20%). The nanoparticle consisting of S-SAMiRNA was observed with a material having a high electron density through a negative staining method. It was confirmed that the nanoparticle observed by TEM had a size similar to that of the nanoparticle measured in Example 3-2.

Example 4

Inhibition of Expression of Target Gene in Tumor Cell Line Using Nanoparticle Consisting of monoSAMiRNA The expression aspect of survivin gene of the transfected tumor cell line was analyzed by using the nanoparticle consisting of monoSAMiRNA prepared by Example 3-2.

Example 4-1

Culture of Tumor Cell Line

Human cervical cancer cell (HeLa) acquired from American type Culture Collection (ATCC) was cultured in EMEM culture medium (ATCC-formulated eagle's minimum essential medium, U.S.A) containing 10% (v/v) fetal bovine serum, 100 units/ml of penicillin and 100 μg/ml of streptomycin, under condition of 37° C. and 5% (v/v) $CO_2$.

Example 4-2

Transformation of Tumor Cell Line Using Nanoparticle Consisting of monoSAMiRNA $1 \times 10^5$ fibroblast cell line cultured by Example 4-1 was cultured in EMEM medium for 18 hours in 12-well plate under condition of 37° C. and 5% (v/v) $CO_2$, and the medium was removed, and the same amount of Opti-MEM medium (GIBCO, USA) for each well was dispensed. 100 μl of Opti-MEM medium and SAMiRNA and mono-SAMiRNA produced by Example 3-2 were added to DPBS at a concentration of 50 μg/ml, and the obtained mixture was freeze-dried under condition of −75° C. and 5 mTorr for 48 hours by the same method as Example 3-1 to produce homogenized nanoparticles. Then, each well of the tumor cell line in which the Opti-MEM is dispensed was treated with a transfection solution at a concentration of 200 nM, and cultured under condition of 37° C. and 5% (v/v) $CO_2$ for the total of 48 hours.

Example 4-3

Relative Quantitative Analysis of mRNA of Survivin Gene cDNA was synthesized by extracting the total RNA from the transfected cell line in Example 4-2 above, and an expression amount of Survivin mRNA was relatively quantified by real-time PCR according to a method disclosed in Korean Patent Laid-Open Publication No. 10-2009-0042297 (see FIG. 17). Sur584 means SAMiRNA having double-stranded oligo RNA sequence (SEQ ID NO: 1) specific to the target gene Survivin for each structure of SAMiRNA, and CONT means SAMiRNA including control group sequence (SEQ ID NO: 2) that does not affect expression of the target gene. A degree of inhibiting expression of mRNA of the target gene was calculated with the expression amount of the target gene of a sample treated with Sur584 with respect to the expression amount of the target gene of a sample treated with CONT through comparative quantification. All of monoSAMiRNAs (n=1 to 4) including Survivin-specific double-stranded oligo RNA had an inhibition effect of target gene expression, and it was observed that from monoSAMiRNA (n=2) in which the hydrophilic material blocks are two or more, the high inhibition effect of target gene expression (about 75% or more of inhibition of expression) was maintained.

Example 5

Preparation of Double-stranded Oligo Structure into which Amine Group and/or Histidine Group is Introduced into Hydrophilic Material

Example 5.1

Preparation of SAMiRNA Including Ethylene Glycol as Hydrophilic Material Monomer In a case of the double-stranded oligo structure including ethylene glycol, particularly, hexamethylene glycol as a hydrophilic material monomer, and $C_{24}$ tetradocosane as a hydrophobic material in the present invention, the double-stranded oligo structure may be represented by Structural Formula (22) below:

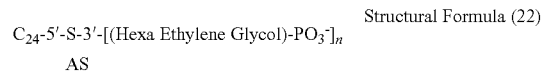

Structural Formula (22)

In Structural Formula (22), $C_{24}$ is tetradocosane which is a hydrophobic material, and n is a repeating unit of hexa ethylene glycol and is the same as being defined in Structural Formula (1) or (2).

In the present Example, a double-stranded oligo RNA structure ([hexa ethylene glycol]$_4$-SAMiRNA) represented by Structural Formula (23) below, wherein n is 4, was prepared:

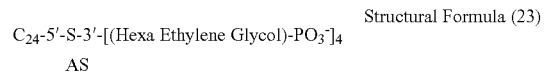

Structural Formula (23)

The Structural Formula (23) is specifically represented by Structural Formula (24) below:

Structural Formula (24)

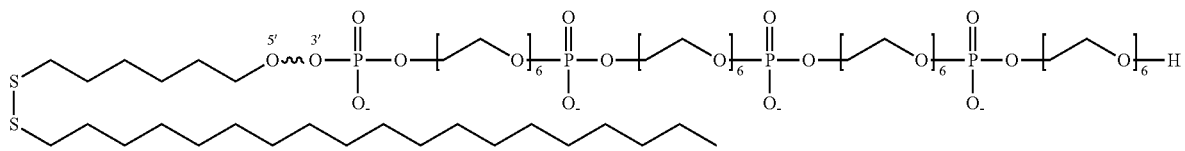

In Structural Formulas (23) and (24), S is a sense strand of siRNA; AS is an antisense strand of siRNA; hexa ethylene glycol is a hydrophilic material; $C_{24}$ is a hydrophobic material and tetradocosane including a disulfide bond; and 5' and 3' mean directivities of the double-stranded oligo RNA end.

The sense strand of siRNA of Structural Formulas (23) and (24) was produced by synthesizing n hexa ethylene glycols having a form of β-cyanoethyl phosphoramidite, based on 3' Uny-CPG produced by Example 1 of Korean Patent Laid-Open Publication No. 10-2012-0119212, as a support, and synthesizing a sense strand of an oligo RNA-hydrophilic material structure to which hexa ethylene glycol is bonded to 3' end by the above-described method in which a phosphodiester bond forming an RNA backbone structure is linked by using RNA β-cyanoethyl phosphoramidite, and binding tetradocosane including a disulfide bond to 5' end, thereby producing the sense strand of the desired RNA-polymer structure. For an antisense strand in which annealing is performed with the sense strand, the antisense strand having a complementary sequence to the sense strand was produced by the above-described reaction.

When the synthesis was completed, the RNA single strand and the RNA-polymer structure synthesized by treating 28% (v/v) ammonia in water bath at 60° C. were separated from CPG and protecting moieties were removed therefrom by a deprotection reaction, respectively. The RNA single strand and the RNA-polymer structure each from which the protecting moiety was removed, were treated with N-methyl pyrrolidone, triethylamine and triethylaminetrihydrofluoride at a volume ratio of 10:3:4, in an oven at 70° C., to remove 2' TBDMS (tert-butyldimethylsilyl).

RNA of the reaction product was separated and purified by HPLC LC918 (Japan Analytical Industry, Japan) equipped with Daisogel C18 (Daiso, Japan) column, and it was confirmed whether or not the purified RNA meets the target base sequence by MALDI-TOF mass spectrometer (Shimadzu, Japan). Then, in order to prepare each double-stranded oligo RNA structure, the sense strand and the antisense strand in an equivalent amount were mixed to each other and put into 1× annealing buffer (30 mM HEPES, 100 mM potassium acetate, 2 mM magnesium acetate (pH 7.0 to 7.5)), followed by reaction in a constant temperature water bath at 90° C. for 3 minutes, and reacted again at 37° C., thereby preparing each double-stranded oligo RNA structure including siRNA having Survivin sequence as the sense strand. It was confirmed by electrophoresis that the produced double-stranded oligo RNA structure was annealed.

Example 5.2

Preparation of SAMiRNA Including Ethylene Glycol into which Amine Group is Introduced, as Hydrophilic Material Monomer A double-stranded oligo RNA structure represented by Structural Formula (25) below in which an amine group is introduced into the hydrophilic material, was prepared.

Structural Formula (25)

The Structural Formula (25) is specifically represented by Structural Formula (26) below:

Structural Formula (26)

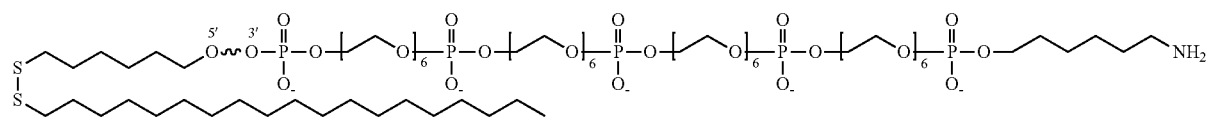

In Structural Formulas (25) and (26), S is a sense strand of siRNA; AS is an antisense strand of siRNA; hexa ethylene glycol is a hydrophilic material; $C_6$ is a linker with 6 carbons connecting [Ethylene Glycol]$_4$ and Amine, $C_{24}$ is a hydrophobic material and tetradocosane including a disulfide bond; and 5' and 3' mean directivities of the double-stranded oligo RNA end.

Further, the hydrophilic material block is connected to a phosphate group at 3' end of the siRNA sense strand.

The sense strand of siRNA of Structural Formulas (25) and (26) was produced by synthesizing 4 hexa ethylene glycols having a form of β-cyanoethyl phosphoramidite, based on CPG including 3' Succinimide derivative, as a support, and synthesizing a sense strand of an oligo RNA-hydrophilic material structure to which hexa ethylene glycol is bonded to 3' end by the above-described method in which a phosphodiester bond forming an RNA backbone structure is linked by using RNA β-cyanoethyl phosphoramidite, and binding tetradocosane including a disulfide bond to 5' end, thereby producing the sense strand of the desired RNA-polymer structure. For an antisense strand in which annealing is performed with the sense strand, the antisense strand having a complementary sequence to the sense strand was produced by the above-described reaction.

When the synthesis was completed, the RNA single strand and the RNA-polymer structure synthesized by treating 28% (v/v) ammonia in water bath at 60° C. were separated from CPG and protecting moieties were removed therefrom by a deprotection reaction, respectively. The RNA single strand and the RNA-polymer structure each from which the protecting moiety was removed, were treated with N-methylpyrolidon, triethylamine and triethylaminetrihydrofluoride at a volume ratio of 10:3:4, in an oven at 70° C., to remove 2' TBDMS (tert-butyldimethylsilyl).

RNA of the reaction product was separated and purified by HPLC LC918 (Japan Analytical Industry, Japan) equipped with Daisogel C18 (Daiso, Japan) column, and it was confirmed whether or not the purified RNA meets the target base sequence by MALDI-TOF mass spectrometer (Shimadzu, Japan). Then, in order to prepare each double-stranded oligo RNA structure, the sense strand and the antisense strand in an equivalent amount were mixed to each other and put into 1× annealing buffer (30 mM HEPES, 100 mM potassium acetate, 2 mM magnesium acetate (pH 7.0 to 7.5)), followed by reaction in a constant temperature water bath at 90° C. for 3 minutes, and reacted again at 37° C., thereby preparing each double-stranded oligo RNA structure including siRNA having Survivin sequence as the sense strand (hereinafter, referred to as SAMiRNA-Survivin, respectively). It was confirmed by electrophoresis that the produced double-stranded oligo RNA structure was annealed.

Example 5.3

Preparation of SAMiRNA Including Ethylene Glycol into which Polyhistidine Group is Introduced, as Hydrophilic Material Monomer A double-stranded oligo RNA structure represented by Structural Formula (27) below in which peptide is introduced into the hydrophilic material, was prepared.

Structural Formula (27)

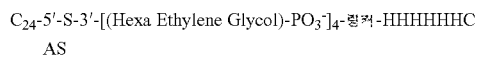

AS

In Structural Formula (27), H is histidine, and C is cystein.

The Structural Formula (27) is specifically represented by Structural Formula (28) below:

Structural Formula (28)

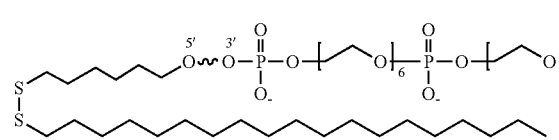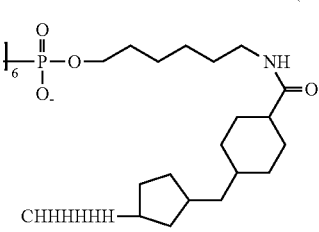

In Structural Formulas (27) and (28), S is a sense strand of siRNA; AS is an antisense strand of siRNA; [Ethylene Glycol]$_4$ is a hydrophilic material; a linker is a link between peptide and SAMiRNA, Peptide is a peptide consisting of HHHHHHC sequence; $C_{24}$ is a hydrophobic material and tetradocosane including a disulfide bond; and 5' and 3' mean directivities of the double-stranded oligo RNA end.

Further, the hydrophilic material block is connected to a phosphate group at 3' end of the siRNA sense strand.

The sense strand of siRNA in Structural Formulas (27) and (28) was prepared by connecting a linker having a functional group (for example: NHSester) bonded to amines and a functional group (for example: maleimide) bonded to thiol (-SH) of peptide with the oligo represented by Structural Formulas (25) and (26) of Example 5-2. Specifically, the linker was bonded to the oligo having the structure of Structural Formulas (25) and (26), and then purified by HPLC or resin. The peptide was bonded to the purified oligo, and purified by HPLC, thereby preparing the sense strand of siRNA. For an antisense strand in which annealing is performed with the sense strand, the antisense strand having a complementary sequence to the sense strand was produced by the above-described reaction. RNA of the reaction product was separated and purified by HPLC LC918 (Japan Analytical Industry, Japan) equipped with Daisogel C18 (Daiso, Japan) column, and it was confirmed whether or not the purified RNA meets the target base sequence by MALDI-TOF mass spectrometer (Shimadzu, Japan). Then, in order to prepare each double-stranded oligo RNA structure, the sense strand and the antisense strand in an equivalent amount were mixed to each other and put into 1× annealing buffer (30 mM HEPES, 100 mM potassium acetate, 2 mM magnesium acetate (pH 7.0 to 7.5)), followed by reaction in a constant temperature water bath at 90° C. for 3 minutes, and reacted again at 37° C. thereby preparing each double-stranded oligo RNA structure including siRNA having Survivin sequence as the sense strand (hereinafter, referred to as SAMiRNA-Survivin, respectively). It was confirmed by electrophoresis that the produced double-stranded oligo RNA structure was annealed.

Example 6

Inhibition of Target Gene Expression in HeLa Cell Line by Nanoparticles Formed of Double-stranded Oligo Polymer Structure (Hexa Ethylene Glycol-SAMiRNA)

A cervical cancer cell line (HeLa) was transformed by using nanoparticles formed of Hexa ethylene glycol-SAMiRNA including siRNA sequences that may reduce Survivin expression amount, and the expression aspect of the target gene was analyzed in the transformed cervical cancer cell line (HeLa) at RNA level.

Example 6-1

Culture of Human Cervical Cancer Cell Line

Human cervical cancer cell line (HeLa) obtained from American Type Culture Collection (ATCC) was cultured under the same condition as Example 5-1.

Example 6-2

Transfection of Hexa Ethylene Glycol-SAMiRNA into which Amine Group is Introduced, into Human Cervical Cancer Cell Line $0.8 \times 10^5$ cervical cancer cell line (HeLa) cultured by Example 6-1 was cultured in EMEM medium for 18 hours in 12-well plate under condition of 37° C. and 5% (v/v) $CO_2$, and the medium was removed, and the same amount of Opti-MEM medium (GIBCO, USA) for each well was dispensed. The obtained mixture was freeze-dried at −75° C. and 5 mTorr condition for hours by the same method as Example 5-1 to produce uniform nanoparticles. Hexa ethylene glycol-SAMiRNA prepared by Example 3-2 was added and dissolved in DPBS at a concentration of 50 μg/ml, and treated in Opti-MEM medium (1 ml) according to concentrations of 50, 100, and 200 nM. Opti-MEM including hexa ethylene glycol-SAMiRNA was dispensed and treated in each well of tumor cell line according to concentration, and the obtained product was cultured under condition of 37° C. and 5% (v/v) $CO_2$, for total 24 hours and 48 hours.

Example 6-3

Relative-Quantitative Analysis of Target Gene mRNA cDNA was produced by extracting total RNA from the transfected cell line by Example 6-2 through the same method as Example 4-3, and an mRNA expression amount of the target gene was subjected to relative quantification by real-time PCR. The inhibition amount of the target gene expression according to treatment of the hexa ethylene glycol-SAMiRNA into which the amine group was introduced, was observed to clearly confirm efficacy of hexa ethylene glycol-SAMiRNA into which the amine group was introduced, as compared to the control group, hexa ethylene glycol-SAMiRNA (FIG. 18).

ADVANTAGEOUS EFFECTS

The oligonucleotide structure according to the present invention may have all of the same hydrophilic material portions, such that problems such as quality control, etc., caused by polydispersity characteristic occurring when a hydrophilic material bonded to the oligonucleotide is a synthetic polymer may be remarkably improved. Further, as compared to the existing purification process using polydispersity hydrophilic materials, the method for preparing the oligonucleotide structure according to the present invention may be simple, may reduce the synthesis cost, and may easily perform material analysis of the oligonucleotide struc-ture. Further, the size of nanoparticles may be regulated by controlling the repetition number of hydrophilic material blocks and hydrophilic material monomers in each hydrophilic material block.

In particular, when the ligand is additionally bonded to the receptor that promotes target cell internalization through receptor-mediated endocytosis (RME) in the oligonucleotide structure according to the present invention, delivery into the target cell is more effectively performed. Further, when the ligand is sugar, together with the targeting effect of the nanoparticles, hydrophilicity which is decreased depending on the repetition number of the hydrophilic material blocks, may be complemented to improve intracellular delivery of the oligonucleotide and to improve an efficacy for controlling gene expression of oligonucleotide.

Further, after the oligonucleotide structure is absorbed into the cell, the oligonucleotide may be easily escaped from the endosome, and may have an effect of inhibiting the decomposition by lysosome, such that higher treatment effect may be obtained by introducing the amine group or the polyhistidine groups into the hydrophilic material block.

From the foregoing, it will be understood by those skilled in the art to which the present invention pertains that the present invention can be carried out in other concrete embodiments without changing the technical spirit or essential feature thereof. In this regard, it should be understood that the aforementioned examples are of illustrative in all aspects but not is limited. The scope of the present invention should be construed to include the meaning and scope of the appended claims, and all the alterations and modified forms which are derived from the equivalent concept thereof, rather than the detailed description.

The invention claimed is:

1. An oligonucleotide structure having a structure represented by the following Structural Formula (1) or Structural Formula (2).

$$Q\text{-}(A_m\text{-}J)_n\text{-}X\text{-}R\text{-}Y\text{-}B \quad \text{Structural Formula (1)}$$

$$Q\text{-}(J\text{-}A_m)_n\text{-}X\text{-}R\text{-}Y\text{-}B \quad \text{Structural Formula (2)}$$

wherein A is a hydrophilic material monomer, B is a hydrophobic material, J is a linker for connecting between m hydrophilic material monomers, or a linker for connecting between m hydrophilic material monomers with oligonucleotides, X and Y are each independently a simple covalent bond or a linker-mediated covalent bond, R is single-stranded or double-stranded oligonucleotide, m is an integer of 1 to 15, and n is an integer of 1 to 10, Q is $(L_i\text{-}Z_j)$ or $P\text{-}J_1\text{-}J_2$, L is a ligand specifically bonded to a receptor that promotes target cell internalization through receptor-mediated endocytosis (RME), Z is a linker that mediates a simple covalent bond or a bond between the hydrophilic material monomer in a hydrophilic material block and the ligand, i represents an integer from 0 to 5, preferably, an integer of 0 to 3, and j means 0 or 1, provided that when i is 0, j is necessarily 0, P means an amine group or a polyhistidine group, and $J_1$ and $J_2$ are independently linkers that mediate a simple covalent bond, or a bond between the amine group or the polyhistidine group with the hydrophilic material.

2. The oligonucleotide structure according to claim 1, wherein R is double stranded oligonucleotides, and sense strand or anti-sense strand has 19 to 31 nucleotides.

3. The oligonucleotide structure according to claim 2, wherein phosphate group is bonded to 5' end of anti-sense strand of double stranded oligonucleotides.

4. The oligonucleotide structure according to claim 3, wherein the phosphate group bonded to 5' end of anti-sense strand is one to three.

5. The oligonucleotide structure according to claim 1, wherein the hydrophobic material has a molecular weight of 250 to 1,000.

6. The oligonucleotide structure according to claim 5, wherein the hydrophobic material is one selected from the group consisting of a steroid derivative, a glyceride derivative, glycerol ether, polypropylene glycol, $C_{12}$ to $C_{50}$ unsaturated or saturated hydrocarbon, diacylphosphatidylcholine, fatty acid, phospholipid and lipopolyamine.

7. The oligonucleotide structure according to claim 6, wherein the steroid derivative is selected from the group consisting of cholesterol, cholestanol, cholic acid, cholesteryl formate, cholestanyl formate, and cholesteryl amine.

8. The oligonucleotide structure according to claim 6, wherein the glyceride derivative is selected from the group consisting of mono-, di- and tri-glyceride.

9. The oligonucleotide structure according to claim 1, wherein the hydrophilic material monomer has a structure represented by the following Compound (1):

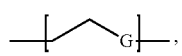

Compound (1)

wherein G is selected from the group consisting of $CH_2$, O, S and NH.

10. The oligonucleotide structure according to claim 1, wherein the linker(J) is selected from group consisting of $PO_3^-$, $SO_3$ and $CO_2$.

11. The oligonucleotide structure according to claim 1, wherein X, Y and Z are respectively non-degradable bond or a degradable bond.

12. The oligonucleotide structure according to claim 11, wherein the non-degradable bond is amide bond or a phosphorylation bond.

13. The oligonucleotide structure according to claim 11, wherein the degradable bond is a disulfide bond, an acid degradable bond, an ester bond, an anhydride bond, a biodegradable bond or an enzymatically degradable bond.

14. The oligonucleotide structure according to claim 1, wherein Q is $(L_i\text{-}Z_j)$, Z is a linker that mediates a bond between the hydrophilic material monomer in a hydrophilic material block and the ligand, and the linker Z comprises hexaethylene glycol.

15. The oligonucleotide structure according to claim 14, wherein the linker Z is Compound (4):

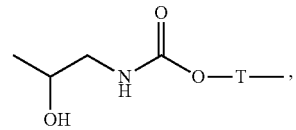

Compound (4)

wherein T refers to 1 to 15 repetitive Compound (1) represented below, and G is selected from the group consisting of $CH_2$, O, S and NH.

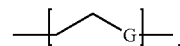

Compound (1)

16. The oligonucleotide structure according to claim 1, wherein Q is $(L_i\text{-}Z_j)$, and has a structure represented by Structural Formula (19) below:

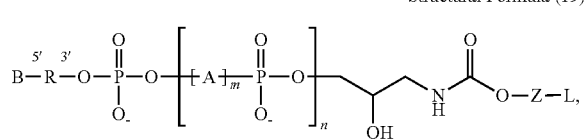

Structural Formula (19)

wherein A, B, R, m, n, Z and L are the same as being defined in Structural Formula (2) of claim 1.

17. The oligonucleotide structure according to claim 1, wherein Q is $(L_i\text{-}Z_j)$, and the ligand (L) is selected from the group consisting of carbohydrate, peptide, and antibody.

18. The oligonucleotide structure according to claim 17, wherein carbohydrate is selected from the group consisting of hexoamine, monosaccharide, disaccharide and polysaccharide.

19. The oligonucleotide structure according to claim 1, wherein Q is $P\text{-}J_1\text{-}J_2$, and P is one selected from the group consisting of primary to tertiary amine groups or polyhistidine group comprising 5 to 8 histidines.

20. The oligonucleotide structure according to claim 19, wherein $J_1$ and $J_2$ are independently selected from the group consisting of simple covalent bond, $C_{2\text{-}12}$ alkyl, alkenyl, alkynyl, $PO_3^-$, $SO_3$, and $CO_2$.

21. A method of preparing single stranded or double stranded oligonucleotide structure according to claim 1 by using a solid support represented by Structural Formula (20) below:

Structural Formula (20)

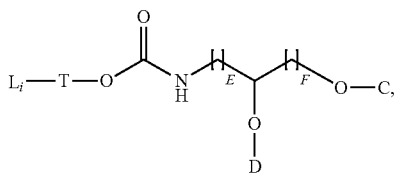

wherein L is a ligand specifically bonded to the receptor that promotes target cell internalization through receptor-mediated endocytosis (RME), T is a compound in which compound (1) is repeated 1 to 15 times (G is selected from the group consisting of $CH_2$, O, S and NH in Compound (1)), Compound (1)

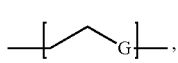

one of C and D refers to solid support, another of C and D refers to Dimethoxytrityl, i is an integer of 0 to 3, and E and F are independently of 1 to 10.

22. The method of claim 21, comprising:
(1) covalently binding a hydrophilic material block to the solid support represented by Structural Formula (20) n-times repeatedly;
(2) synthesizing a single-stranded oligonucleotide based on the solid support to which the hydrophilic material block is bonded;
(3) covalently binding a hydrophobic material to 5' end of oligonucleotide to which the hydrophilic material block is bonded; and
(4) separating the oligonucleotide structure from the solid support.

23. The method of claim 21, comprising:
(1) covalently binding a hydrophilic material block to the solid support represented by Structural Formula (20) n-times repeatedly;
(2) synthesizing a single-stranded RNA based on the solid support to which the hydrophilic material block is bonded;
(3) covalently binding a hydrophobic material to 5' end of RNA to which the hydrophilic material block is bonded;
(4) separating the RNA-polymer structure and a single-stranded RNA having a complementary sequence thereto from the solid support; and
(5) forming the double-stranded oligonucleotide by annealing the RNA-polymer structure and the single-stranded RNA having a complementary sequence thereto.

24. The method of claim 22, wherein single-stranded oligonucleotide complementary to the single-stranded oligonucleotide of the step (2) has a phosphate group, bonded to 5' end of the single-stranded oligonucleotide.

25. Nanoparticle(s) comprising the oligonucleotide structure according to claim 1.

26. The nanoparticle(s) according to claim 25, wherein the nanoparticle(s) is lyophilized.

27. A pharmaceutical composition comprising the oligonucleotide structure according to claim 1.

28. A pharmaceutical composition comprising the nanoparticle(s) according to claim 25.

29. A method of controlling an expression of gene in vitro or in vivo by using the oligonucleotide structure according to claim 1.

30. A method of controlling an expression of gene in vitro or in vivo by using the nanoparticle(s) according to claim 25.

31. A pharmaceutical composition comprising the nanoparticle(s) according to claim 26.

32. A method of controlling an expression of gene in vitro or in vivo by using the nanoparticle(s) according to claim 26.

* * * * *

UNITED STATES PATENT AND TRADEMARK OFFICE
CERTIFICATE OF CORRECTION

PATENT NO. : 10,030,243 B2
APPLICATION NO. : 14/902563
DATED : July 24, 2018
INVENTOR(S) : Han Oh Park et al.

It is certified that error appears in the above-identified patent and that said Letters Patent is hereby corrected as shown below:

In the Specification

Column 5, Line 41: "2.04~42.02" should be --2.04~2.02--.

Column 5, Line 58: "3.9~43.85" should be --3.94~3.85--.

Column 5, Line 59: "3.4~03.24" should be --3.40~3.24--.

Column 5, Line 65: "7.4~07.20" should be --7.40~7.20--.

Column 5, Line 66: "5.2~25.20" should be --5.22~5.20--.

Column 6, Line 1: "3.5~3.49" should be --3.51~3.49--.

Column 6, Line 2: "2.1~12.09" should be --2.11~2.09--.

Column 6, Line 8: "7.43~0.38" should be --7.43~.38--.

Signed and Sealed this
Fourth Day of September, 2018

Andrei Iancu
*Director of the United States Patent and Trademark Office*

SEQUENCE LISTING

```
<160> NUMBER OF SEQ ID NOS: 2

<210> SEQ ID NO 1
<211> LENGTH: 18
<212> TYPE: RNA
<213> ORGANISM: Artificial Sequence
<220> FEATURE:
<223> OTHER INFORMATION: sense strand of double-stranded oligo RNA to
      Survivin

<400> SEQUENCE: 1
aaggagauca acauuuuc                                                  18

<210> SEQ ID NO 2
<211> LENGTH: 18
<212> TYPE: RNA
<213> ORGANISM: Artificial Sequence
<220> FEATURE:
<223> OTHER INFORMATION: sense strand of double-stranded oligo RNA used
      as a control group

<400> SEQUENCE: 2
cuuacgcuga guacuucg                                                  18
```